United States Patent
Chennamsetty et al.

(10) Patent No.: US 8,747,848 B2
(45) Date of Patent: Jun. 10, 2014

(54) IMMUNOGLOBULINS WITH REDUCED AGGREGATION

(75) Inventors: Naresh Chennamsetty, Cambridge, MA (US); Bernhard Helk, Basel (CH); Veysel Kayser, Cambridge, MA (US); Bernhardt Trout, Cambridge, MA (US); Vladimir Voynov, Cambridge, MA (US)

(73) Assignees: Novartis AG, Basel (CH); Massachusetts Institute of Technology, Cambridge, MA (US)

( * ) Notice: Subject to any disclaimer, the term of this patent is extended or adjusted under 35 U.S.C. 154(b) by 453 days.

(21) Appl. No.: 13/000,351

(22) PCT Filed: Jun. 19, 2009

(86) PCT No.: PCT/US2009/047948
§ 371 (c)(1),
(2), (4) Date: Sep. 20, 2011

(87) PCT Pub. No.: WO2009/155513
PCT Pub. Date: Dec. 23, 2009

(65) Prior Publication Data
US 2012/0003211 A1   Jan. 5, 2012

Related U.S. Application Data

(60) Provisional application No. 61/074,466, filed on Jun. 20, 2008, provisional application No. 61/151,368, filed on Feb. 10, 2009.

(51) Int. Cl.
*A61K 38/00* (2006.01)

(52) U.S. Cl.
USPC .................... 424/133.1; 435/328; 530/387.3

(58) Field of Classification Search
None
See application file for complete search history.

(56) References Cited

U.S. PATENT DOCUMENTS

| 6,277,375 B1 | 8/2001 | Ward |
| 2005/0244403 A1 | 11/2005 | Lazar et al. |
| 2007/0202098 A1* | 8/2007 | Lazar et al. ................ 424/133.1 |

FOREIGN PATENT DOCUMENTS

| EP | 1810979 A | 7/2007 |
| EP | 2006380 A1 | 12/2008 |
| WO | WO-03/074679 A | 9/2003 |
| WO | WO 03074679 A2 * | 9/2003 |
| WO | WO-2004/001007 A | 12/2003 |
| WO | WO-2005/045442 A | 5/2005 |
| WO | WO-2006/034488 A2 | 3/2006 |
| WO | WO-2007/103288 A2 | 9/2007 |
| WO | WO-2007/109221 A | 9/2007 |

OTHER PUBLICATIONS

Jespers et al (Nature Biotechnology, 2004, 22:1161-1165).*
Burgess et al (J Cell Biol, 1990, 111:2129-2138).*
Lazar et al (Mol Cell Biol, 1998, 8:1247-1252).*
Nelson et al (Principles of Biochemistry, 2000, p. 1-1152).*
Thermo (Antibody structure and Classes, 2003, p. 1-5).*
Gokarn et al (Journal of Pharmaceutical Sciences, 2008, 97:3051-3066).*
Chennamsetty et al. (Aug. 14, 2009). "Aggregation-prone motifs in human immunoglobulin G" J Mol Biol 391(2):404-413.
International Preliminary Report on Patentability mailed Feb. 12, 2013, for PCT/US2009/047948, 13 pages.
International Search Report and Written Opinion mailed Jan. 25, 2013, for PCT/US2009/047948, 23 pages.
Yanling et al. (Feb. 2008). "The effect of a point mutation on the stability of IgG4 as monitored by analytical ultracentrifugation," J Pharm Sci 97(2):960-969.
Cellmer et al. (May 17, 2007). "Protein aggregation in silico," Trends in Biotechnology 25(6):254-257.
Chennamsetty, N. et al. (Jul. 2009). "Design of therapeutic proteins with enhanced stability," Proceedings of the National Academy of Sciences of the United States of America 106(29):11937-11942.
De Groot, N.S. et al. (Sep. 30, 2005). "Prediction of hot spots of aggregation in disease-linked polypeptides," BMC Structural Biology 5(1):18.
International Search Report and Written Opinion mailed Nov. 30, 2009, for PCT Application No. PCT/US2009/047954 filed Jun. 19, 2009, 20 pages.
Pawar, A.P. et al. (Jul. 8, 2005). "Prediction of 'Aggregate-prone' and 'Aggregate-susceptible' Regions in Proteins Associated with Neurodegenerative Diseases," Journal of Molecular Biology 350(2):379-392.
Spassov, V. et al. (1995). "The optimization of protein-solvent interactions: Thermostability and the role of hydrophobic and electrostatic interactions," Protein Science 4(8):1516-1527.
Abraham et al. (1987). "Extension of the fragment method to calculate amino acid zwitterion and side chain partition coefficients," Proteins: Structure, function, and genetics 130-152, p. 148.
Black et al. (1991). "Development of hydrophobicity parameters to analyze proteins which bear post- or cotranslational modifications," Anal Biochem 193:72-82.
Brard et al. (Sep. 6, 1999) "Somatic mutation and light chain rearrangement generate autoimmunity in anti-single-stranded DNA transgenic MRUIpr mice" Journal of Experimental Medicine 190(5):691-704.
International search report mailed Jan. 12, 2011, for PCT/US2010/037517 filed Jun. 4, 2010, 8 pages.
Junutula et al. (Aug. 1, 2008) "Site-specific conjugation of a cytotoxic drug to an antibody improves the therapeutic index" Nature Biotechnology 26(8):925-932.
Junutula et al. (Jan. 14, 2008). "Rapid identification of reactive cysteine residues for site-specific labeling of antibody-Fabs" Journal of Immunological Methods, 332(1-2):41-52.
Kellog et al. (1991). "HINT: a new method of empirical hydrophobic field calculation for CoMFA," J Computer-Aided Molec Des 5:545-552.

(Continued)

Primary Examiner — Sean Aeder
Assistant Examiner — Julie Wu
(74) Attorney, Agent, or Firm — Morrison & Foerster LLP

(57) ABSTRACT

The present disclosure relates to immunoglobulins with reduced aggregation and compositions, methods of generating such immunoglobulins with computational tools and methods of using such immunoglobulins particularly in the treatment and prevention of disease.

18 Claims, No Drawings

(56) References Cited

OTHER PUBLICATIONS

Lee et al. (1971). "The interpretation of protein structures: estimation of static accessibility," J Mol Biol 55:379-400.

Lyons et al. (Jan. 1, 1990) "Site-specific attachment to recombinant antibodies via introduced surface cysteine residues" Protein Engineering 3(8):703-708.

Stimmel et al. (Sep. 29, 2000) "Site-specific conjugation on serine-cysteine variant monoclonal antibodies" Journal of Biological Chemistry 275(39):30445-30450.

Voynov et al. (Feb. 17, 2010) "Design and application of antibody cysteine variants." Bioconjugate Chemistry 21(2):385-392.

Wesson et al. (1992). "Atomic solvation parameters applied to molecular dynamics of proteins in solution," Protein Sci 1(2):227-235.

\* cited by examiner

IMMUNOGLOBULINS WITH REDUCED AGGREGATION

CROSS REFERENCE TO RELATED APPLICATIONS

This application is a U.S. National Phase patent application of PCT/US2009/047948, filed Jun. 19, 2009, which claims priority to U.S. Provisional patent application Ser. No. 61/074,466 filed Jun. 20, 2008 and U.S. Provisional patent application Ser. No. 61/151,368 filed Feb. 10, 2009, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 619672000100SeqList.txt, date recorded: Dec. 20, 2010, size: 13 KB).

FIELD OF THE INVENTION

The present disclosure relates to improved immunoglobulins having reduced aggregation.

BACKGROUND

Understanding and controlling protein stability has been a coveted endeavor to Biologists, Chemists, and Engineers. The first link between amino acid substitution and disease (Ingram. Nature. 1957, 180(4581):326-8.) offered a new and essential perspective on protein stability in health and disease. The recent tremendous increase of protein-based pharmaceuticals, particularly immunoglobulin based pharmaceuticals, has created a new challenge. Therapeutic proteins are stored in liquid for several months at very high concentrations. The percent of non-monomeric species increases with time. As aggregates form, not only the efficacy of the product decreases, but side effects such as immunological response upon administration may occur. Assuring stability of protein pharmaceuticals for the shelf-life of the product is imperative.

Because of their potential in the cure of various diseases, antibodies currently constitute the most rapidly growing class of human therapeutics (Carter. Nature Reviews Immunology. 2006, 6(5), 343). Since 2001, their market has been growing at an average yearly growth rate of 35%, the highest rate among all categories of biotech drugs (S. Aggarwal. Nature. BioTech. 2007, 25 (10) 1097).

Therapeutic immunoglobulins are prepared and stored in aqueous solutions at high concentrations, as required for the disease treatment. However, these immunoglobulins are thermodynamically unstable under these conditions and degrade due to aggregation. The aggregation in turn leads to a decrease in antibody activity making the drug ineffective and can even generate an immunological response. Thus, there is an urgent need to generate therapeutic immunoglobulins that are less prone to aggregation.

Numerous existing approaches for preventing immunoglobulin aggregation employ the use of additives in protein formulations. This is different from the direct approach described herein where immunoglobulin itself is modified based on the aggregation prone regions predicted from molecular simulations. Additives commonly used in antibody stabilization are salts of nitrogen-containing bases, such as arginine, guanidine, or imidazole (EP0025275). Other suitable additives for stabilization are polyethers (EPA0018609), glycerin, albumin and dextran sulfate (U.S. Pat. No. 4,808, 705), detergents and surfactants such as polysorbate based surfactants (Publication DE2652636, and Publication GB2175906 (UK Pat. Appl. No. GB8514349)), chaperones such as GroEL (Mendoza. Biotechnol. Tech. 1991, (10) 535-540), citrate buffer (WO9322335) or chelating agents (WO9115509). Although these additives enable proteins to be stabilized to some degree in solution, they suffer from certain disadvantages such as the necessity of additional processing steps for additive removal.

Optimized immunoglobulin variants have been generated to improve other characteristics such as binding of the Fc receptor. By way of example, a genus of two hundred and sixteen antibody variants were generated (including L234 and L235 mutant species) and tested for the effect upon binding to FcγRIIIa and FcγRIIb as disclosed in US Pat. Publ. 2004/0132101 (Lazar et al.). However, Lazar et al. did not test any of the antibody variants for their propensity for aggregation.

Thus, there is a need for improved immunoglobulin compositions, such as antibody therapeutics, that are directly stabilized without the use of additives.

SUMMARY

Described herein are improved immunoglobulins which exhibit reduced aggregation and/or enhanced stability that meet this need.

Thus one aspect includes modified and/or isolated immunoglobulins that have a reduced propensity for aggregation comprising at least one aggregation reducing mutation at a residue in a conserved domain of the immunoglobulin that (i) has a Spatial-Aggregation-Propensity (5 Å radius sphere) of at least 0.15, or (ii) has an Spatial-Aggregation-Propensity (5 Å radius sphere) of greater than 0.0 and is within 5 Å of a residue having a Spatial-Aggregation-Propensity (5 Å radius sphere) of at least 0.15, wherein the at least one aggregation reducing mutation is a substitution with an amino acid residue that lowers the Spatial-Aggregation-Propensity (5 Å radius sphere) of the residue as compared to the unmutated immunoglobulin and the propensity for aggregation that is reduced is aggregation between immunoglobulin molecules in a concentrated, liquid solution. In certain embodiments, the at least one aggregation reducing mutation is not at a residue corresponding to Kabat residue 234(hinge) or 235(hinge) in IgG1 based upon alignment with the IgG1 sequence. In certain embodiments that may be combined with the preceding embodiments, the immunoglobulin has a second aggregation reducing mutation at a residue that (i) has a Spatial-Aggregation-Propensity (5 Å radius sphere) of at least 0.15, or (ii) has an Spatial-Aggregation-Propensity (5 Å radius sphere) of greater than 0.0 and is within 5 Å of a residue having a Spatial-Aggregation-Propensity (5 Å radius sphere) of at least 0.15, wherein the second aggregation reducing mutation is a substitution with an amino acid residue that is a substitution with an amino acid residue that lowers the Spatial-Aggregation-Propensity (5 Å radius sphere) of the residue as compared to the unmutated immunoglobulin. In certain embodiments that may be combined with the preceding embodiments having a second aggregation reducing mutation, the aggregation reducing mutation and the second aggregation reducing mutation are at least 5 Å, at least 10 Å, at least 15 Å, or at least 20 Å apart. In certain embodiments that may be combined with the preceding embodiments having a second aggregation reducing mutation, the aggregation reducing mutation and the second aggregation reducing mutation are in different aggregation motifs. In certain embodiments that may be combined with any of the preceding embodiments, the aggregation reducing mutation is a substitution with an amino acid residue that is less hydrophobic than the residue in the unmodified immunoglobulin. In certain embodiments that may be combined with the preceding embodiments, the aggregation reducing mutation is a substitution with an amino acid residue selected from the group consisting of lysine, arginine, histidine, glutamate, aspartate, glutamine, and asparagine. In certain embodiments that may be combined with the preceding embodiments, the aggregation reducing mutation is a substitution with an amino acid residue selected from the group consisting of lysine, arginine, and histidine. In certain embodiments that may be combined with the preceding embodiments, the aggregation reducing mutation is a substitution with a lysine residue. In certain embodiments that may be combined with the preceding embodiments, the Spatial-Aggregation-Propensity (5 Å radius sphere) is calculated using the Black Mould hydrophobicity scale normalized so that glycine equals 0. In certain embodiments that may be combined with the preceding embodiments, the immunoglobulin is an IgG1, an IgG2, an IgG3, or an IgG4. In certain embodiments that may be combined with the preceding embodiments, the immunoglobulin is an IgG1. In certain embodiments that may be combined with the preceding embodiments, the immunoglobulin has a human $C_{H1}$ domain. In certain embodiments that may be combined with the preceding embodiments, the immunoglobulin has a human $C_{H2}$ domain. In certain embodiments that may be combined with the preceding embodiments, the immunoglobulin has a human $C_{H3}$ domain. In certain embodiments that may be combined with the preceding embodiments, the immunoglobulin has a human $C_L$ domain. In certain embodiments that may be combined with the preceding embodiments, the immunoglobulin has a binding affinity for a target antigen and the binding affinity for the target antigen is at least seventy percent, at least eighty percent, at least ninety percent, at least one hundred percent, or at least one hundred five percent of the binding affinity of the unmutated immunoglobulin for the target antigen. In certain embodiments that may be combined with the preceding embodiments, the concentrated, liquid solution is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml.

Another aspect includes a modified or isolated immunoglobulin that has a reduced propensity for aggregation comprising at least one aggregation reducing mutation at a residue selected from the group consisting of residues from an aggregation motif 1: 174($C_{H1}$), 175($C_{H1}$), and 181($C_{H1}$); an aggregation motif 2: 226(hinge), 227(hinge), 228(hinge), 229(hinge), 230(hinge), 231(hinge), and 232(hinge); an aggregation motif 3: 234(hinge) and 235(hinge); an aggregation motif 4: 252($C_{H2}$), and 253($C_{H2}$); an aggregation motif 5: 282($C_{H2}$); an aggregation motif 6: 291($C_{H2}$); an aggregation motif 7: 296($C_{H2}$); an aggregation motif 8: 308($C_{H2}$) and 309($C_{H2}$); an aggregation motif 9: 328($C_{H2}$), 329($C_{H2}$), 330($C_{H2}$), and 331($C_{H2}$); an aggregation motif 10: 395($C_{H3}$), 396($C_{H3}$), 397($C_{H3}$), 398($C_{H3}$), and 404($C_{H3}$); an aggregation motif 11: 443($C_{H3}$); an aggregation motif 12: 110($C_L$) and 111($C_L$); an aggregation motif 13: 153($C_L$) and 154($C_L$); and an aggregation motif 14: 201($C_L$), wherein the at least one aggregation reducing mutation is a substitution with an amino acid residue that is less hydrophobic than the residue in the unmodified immunoglobulin and the propensity for aggregation that is reduced is aggregation between immunoglobulin molecules in a concentrated, liquid solution; and wherein the residue numbers are the corresponding Kabat residue numbers in IgG1 based upon alignment with the IgG1 sequence. In certain embodiments, the at least one aggregation reducing mutation residue is selected from the group consisting of residues from an aggregation motif 1: 175($C_{H1}$); an aggregation motif 2: 227(hinge), 228(hinge), and 230(hinge); an aggregation motif 3: 234(hinge) and 235(hinge); an aggregation motif 4: 253($C_{H2}$); an aggregation motif 5: 282($C_{H2}$); an aggregation motif 6: 291($C_{H2}$); an aggregation motif 7: 296($C_{H2}$); an aggregation motif 8: 309($C_{H2}$); an aggregation motif 9: 329($C_{H2}$) and 330($C_{H2}$); an aggregation motif 10: 395($C_{H3}$) and 398($C_{H3}$); an aggregation motif 11: 443($C_{H3}$); an aggregation motif 12: 110($C_L$); an aggregation motif 13: 154($C_L$); and an aggregation motif 14: 201($C_L$). In certain embodiments that may be combined with the preceding embodiments, the aggregation reducing mutation is not residue 234(hinge) or 235(hinge). In certain embodiments that may be combined with the preceding embodiments, the aggregation reducing mutation residue is 234(hinge), 235(hinge), 253($C_{H2}$), or 309($C_{H2}$). In certain embodiments that may be combined with the preceding embodiments, the aggregation reducing mutation residue is 253($C_{H2}$) or 309($C_{H2}$). In certain embodiments that may be combined with any of the preceding embodiments, the immunoglobulin has a second aggregation reducing mutation at a hydrophobic residue that (i) has a Spatial-Aggregation-Propensity of at least 0.15, or (ii) is within 5 Å of a residue having a Spatial-Aggregation-Propensity of at least 0.15, wherein the at least one aggregation reducing mutation is a substitution with an amino acid residue that is less hydrophobic than the residue in the unmodified immunoglobulin. In certain embodiments that may be combined with the preceding embodiments having a second aggregation reducing mutation, the aggregation reducing mutation and the second aggregation reducing mutation are at least 5 Å, at least 10 Å, at least 15 Å, or at least 20 Å apart. In certain embodiments that may be combined with any of the preceding embodiments having a second aggregation reducing mutation, the aggregation reducing mutation and the second aggregation reducing mutation are in different aggregation motifs. In certain embodiments that may be combined with any of the preceding embodiments, the immunoglobulin has at least fourteen aggregation reducing mutations wherein each aggregation reducing mutation is selected from a different aggregation motif. In certain embodiments that may be combined with any of the preceding embodiments, the aggregation reducing mutation is substitution with an amino acid residue selected from the group consisting of lysine, arginine, histidine, glutamate, aspartate, glutamine, and asparagine. In certain embodiments that may be combined with any of the preceding embodiments, the aggregation reducing mutation is substitution with an amino acid residue selected from the group consisting of lysine, arginine, and histidine. In certain embodiments that may be combined with any of the preceding embodiments, the aggregation reducing mutation is substitution with a lysine residue. In certain embodiments that may be combined with the preceding embodiments, the Spatial-Aggregation-Propensity (5 Å radius sphere) is calculated using the Black Mould hydrophobicity scale normalized so that glycine equals 0. In certain embodiments that may be combined with any of the preceding embodiments, the immunoglobulin is an IgG1, an IgG2, an IgG3, or an IgG4. In certain embodiments that may be combined with any of the preceding embodiments, the immunoglobulin comprises an IgG1. In certain embodiments that may be combined with any of the preceding embodiments, the immunoglobulin has a human $C_{H1}$ domain. In certain embodiments that may be combined with any of the preceding embodiments, the immunoglobulin has a human $C_{H2}$ domain. In certain embodiments that may be combined with any of the preceding embodiments, the immunoglobulin has a human $C_{H3}$ domain. In certain embodiments that may be combined with any of the preceding embodiments, the immunoglobulin has a human $C_L$ domain. In certain embodiments that may be combined with any of the preceding embodiments, the immunoglobulin has a binding affinity for a target antigen and the binding affinity for the target antigen is at least seventy percent, at least eighty percent, at least ninety percent, at least one hundred percent, or at least one hundred five percent of the binding affinity of the unmutated immunoglobulin for the target antigen. In certain embodiments that may be combined with the preceding embodiments, the concentrated, liquid solution is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml.

Another aspect includes modified immunoglobulin formulations that can be made up of immunoglobulin of either of the preceding aspects and any and all combinations of the preceding embodiments at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin is at a concentration of greater than the concentration at which the unmutated immunoglobulin aggregates with itself in a concentrated, liquid solution under the same conditions. In certain embodiments that may be combined with the preceding embodiments, at least eighty percent, at least eighty-five percent, at least ninety percent, at least ninety-five percent, at least ninety-six percent, at least ninety-seven percent, at least ninety-eight percent, or at least ninety-nine percent of the modified immunoglobulin is non-aggregated monomer. In certain embodiments that may be combined with any of the preceding embodiments, the formulation includes a pharmaceutically acceptable excipient. In certain embodiments that may be combined with any of the preceding embodiments, the immunoglobulin formulation shows at least five percent, at least ten percent, at least fifteen percent, at least twenty percent, at least twenty-five percent, at least thirty percent, at least thirty-five percent, at least forty percent, or at least fifty percent less aggregate after twenty four hours of accelerated aggregation as compared to the unmutated immunoglobulin under the same conditions. In certain embodiments that may be combined with the preceding embodiments, the aggregation is measured by SEC-HPLC. In certain embodiments that may be combined with any of the preceding embodiments, the immunoglobulin formulation is substantially free of any additive that reduces aggregation of immunoglobulins. In certain embodiments that may be combined with any of the preceding embodiments, the immunoglobulin formulation is substantially free of free histidine, saccharides and polyols.

Yet another aspect includes isolated or recombinant polynucleotides that encode immunoglobulin of either of the preceding modified immunoglobulin aspects and any and all combinations of the preceding embodiments. In certain embodiments, the polynucleotide is in a vector. In certain embodiments, the vector is an expression vector. In certain embodiments that may be combined with the preceding embodiments, an inducible promoter is operably linked to the polynucleotide. Another aspect includes host cells with the vector of either of the preceding embodiments. In certain embodiments, the host cells are capable of expressing the immunoglobulin encoded by the polynucleotide.

Another aspect includes methods of producing an immunoglobulin with a reduced aggregation propensity comprising providing a culture medium comprising the host cell of the preceding aspect and placing the culture medium in conditions under which the immunoglobulin is expressed. In certain embodiments, the methods include an additional step of isolating the immunoglobulin expressed.

Another aspect includes methods for reducing the aggregation propensity of an immunoglobulin in a highly concentrated pharmaceutical formulation comprising providing an immunoglobulin that is prone to aggregation; substituting a residue in a conserved domain of the immunoglobulin that (i) has a Spatial-Aggregation-Propensity of at least 0.15, or (ii) has an Spatial-Aggregation-Propensity (5 Å radius sphere) of greater than 0.0 and is within 5 Å of a residue having a Spatial-Aggregation-Propensity of at least 0.15, with an amino acid residue that lowers the Spatial-Aggregation-Propensity (5 Å radius sphere), and generating a highly concentrated, liquid formulation of the modified immunoglobulin wherein the modified immunoglobulin concentration is at least 20 mg/ml, at least 30 mg/ml, at least 40 mg/ml, at least 50 mg/ml, at least 75 mg/ml, at least 100 mg/ml, at least 125 mg/ml, or at least 150 mg/ml, and wherein the aggregation propensity that is reduced is aggregation between immunoglobulin molecules in a concentrated, liquid solution.

Another aspect includes uses of either of the preceding modified immunoglobulin aspects and any and all combinations of the preceding embodiments in the preparation of a medicament comprising a highly concentrated liquid formulation wherein the modified immunoglobulin concentration is at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the use of the medicament is for the treatment of autoimmune diseases, immunological diseases, infectious diseases, inflammatory diseases, neurological diseases, and oncological and neoplastic diseases including cancer. In certain embodiments, the use of the medicament is for the treatment of congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, breast cancer, lung cancer, kidney cancer and rectal cancer; bone metastasis, bone pain management, and humoral malignant hypercalcemia, ankylosing spondylitisa and other spondyloarthropathies; transplantation rejection, viral infections, hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplamacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, and tumors of the vascular system (angiosarcoma and hemangiopericytoma), osteoporosis, hepatitis, HIV, AIDS, spondylarthritis, rheumatoid arthritis, inflammatory bowel diseases (IBD), sepsis and septic shock, Crohn's Disease, psoriasis, schleraderma, graft versus host disease (GVHD), allogenic islet graft rejection, hematologic malignancies, such as multiple myeloma (MM), myelodysplastic syndrome (MDS) and acute myelogenous leukemia (AML), inflammation associated with tumors, peripheral nerve injury or demyelinating diseases. In certain embodiments, the use of the medicament is for the treatment of plaque psoriasis, ulcerative colitis, non-Hodgkin's lymphoma, breast cancer, colorectal cancer, juvenile idiopathic arthritis, macular degeneration, respiratory syncytial virus, Crohn's disease, rheumatoid arthritis, psoriatic arthritis, ankylosing spondylitis, osteoporosis, treatment-induced bone loss, bone metastases, multiple myeloma, Alzheimer's disease, glaucoma, and multiple sclerosis. In certain embodiments that may be combined with any of the preceding embodiments, the use of the medicament further comprises a pharmaceutically acceptable excipient. In certain embodiments that may be combined with any of the preceding embodiments, the immunoglobulin in the medicament shows at least five percent, at least ten percent, at least fifteen percent, at least twenty percent, at least twenty-five percent, at least thirty percent, at least thirty-five percent, at least forty percent, or at least fifty percent less aggregate after twenty four hours of accelerated aggregation as compared to the unmutated immunoglobulin under the same conditions. In certain embodiments, the aggregation is measured by SEC-HPLC. In certain embodiments that may be combined with any of the preceding embodiments, the medicament is substantially free of any additive that reduces aggregation of immunoglobulins. In certain embodiments that may be combined with any of the preceding embodiments, the medicament is substantially free of free histidine, saccharides and polyols.

Another aspect includes uses of either of the preceding modified immunoglobulin aspects and any and all combinations of the preceding embodiments as a non-aggregating pharmaceutical active ingredient.

Another aspect includes pharmaceutical compositions that include an immunoglobulin of either of the preceding aspects and any and all combinations of the preceding embodiments and a pharmaceutically acceptable excipient. In certain embodiments, the immunoglobulin is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin is at a concentration of greater than the concentration at which the unmutated immunoglobulin aggregates with itself in a concentrated, liquid solution under the same conditions. In certain embodiments that may be combined with the preceding embodiments, at least eighty percent, at least eighty-five percent, at least ninety percent, at least ninety-five percent, at least ninety-six percent, at least ninety-seven percent, at least ninety-eight percent, or at least ninety-nine percent of the modified immunoglobulin is non-aggregated monomer. In certain embodiments that may be combined with any of the preceding embodiments, the immunoglobulin formulation shows at least five percent, at least ten percent, at least fifteen percent, at least twenty percent, at least twenty-five percent, at least thirty percent, at least thirty-five percent, at least forty percent, or at least fifty percent less aggregate after twenty four hours of accelerated aggregation as compared to the unmutated immunoglobulin under the same conditions. In certain embodiments that may be combined with the preceding embodiments, the aggregation is measured by SEC-HPLC. In certain embodiments that may be combined with any of the preceding embodiments, the immunoglobulin formulation is substantially free of any additive that reduces aggregation of immunoglobulins. In certain embodiments that may be combined with any of the preceding embodiments, the immunoglobulin formulation is substantially free of free histidine, saccharides and polyols.

Another aspect includes a modified or isolated immunoglobulin that has a reduced propensity for aggregation comprising at least one aggregation reducing mutation at a residue selected from the group consisting of 235(hinge), 241($C_{H2}$), 243($C_{H2}$), 282($C_{H2}$), and 309($C_{H2}$), wherein if residue 235 is selected, it is mutated to a glutamate or a serine, if residue 282 is selected it is mutated to a lysine, and if residue 309 is selected, it is mutated to a lysine, and wherein the at least one aggregation reducing mutation is a substitution with an amino acid residue that is less hydrophobic than the residue in the unmodified immunoglobulin and the propensity for aggregation that is reduced is aggregation between immunoglobulin molecules in a concentrated, liquid solution; and wherein the residue numbers are the corresponding Kabat residue numbers in IgG1 based upon alignment with the IgG1 sequence. In certain embodiments, the at least one aggregation reducing mutation is a mutation of residue 241 to serine, and the modified or isolated immunoglobulin further comprises a second aggregation reducing mutation of residue 243 to serine. In certain embodiments, the at least one aggregation reducing mutation is a mutation of residue 241 to tyrosine, and the modified or isolated immunoglobulin further comprises a second aggregation reducing mutation of residue 243 to tyrosine. In certain embodiments, the at least one aggregation reducing mutation is a mutation of residue 282 to lysine, and the modified or isolated immunoglobulin further comprises a second and a third aggregation reducing mutation, wherein the second aggregation reducing mutation is a mutation of residue 235 to lysine and the third aggregation reducing mutation is a mutation of residue 309 to lysine. In certain embodiments, the immunoglobulin has a second aggregation reducing mutation at a hydrophobic residue, wherein the at least one aggregation reducing mutation is a substitution with an amino acid residue that is less hydrophobic than the residue in the unmodified immunoglobulin. In certain embodiments that may be combined with the preceding embodiments having a second aggregation reducing mutation, the second aggregation reducing mutation (i) has a Spatial-Aggregation-Propensity of at least 0.15, or (ii) is within 5 Å of a residue having a Spatial-Aggregation-Propensity of at least 0.15. In certain embodiments that may be combined with the preceding embodiments having a second aggregation reducing mutation, the immunoglobulin has a third aggregation reducing mutation that (i) has a Spatial-Aggregation-Propensity of at least 0.15, or (ii) is within 5 Å of a residue having a Spatial-Aggregation-Propensity of at least 0.15, wherein the third aggregation reducing mutation is a substitution with an amino acid residue that is less hydrophobic than the residue in the unmodified immunoglobulin. In certain embodiments that may be combined with the preceding embodiments having a second aggregation reducing mutation, the aggregation reducing mutation and the second aggregation reducing mutation are at least 5 Å, at least 10 Å, at least 15 Å, or at least 20 Å apart. In certain embodiments that may be combined with any of the preceding embodiments having a second aggregation reducing mutation, the aggregation reducing mutation and the second aggregation reducing mutation are in different aggregation motifs. In certain embodiments that may be combined with any of the preceding embodiments, the immunoglobulin has at least fourteen aggregation reducing mutations wherein each aggregation reducing mutation is selected from a different aggregation motif. In certain embodiments that may be combined with any of the preceding embodiments, the aggregation reducing mutation is substitution with an amino acid residue selected from the group consisting of lysine, arginine, histidine, glutamate, aspartate, glutamine, asparagine, tyrosine, and serine. In certain embodiments that may be combined with any of the preceding embodiments, the aggregation reducing mutation is substitution with an amino acid residue selected from the group consisting of lysine, serine, glutamate, and tyrosine. In certain embodiments that may be combined with the preceding embodiments, the Spatial-Aggregation-Propensity (5 Å radius sphere) is calculated using the Black Mould hydrophobicity scale normalized so that glycine equals 0. In certain embodiments that may be combined with any of the preceding embodiments, the immunoglobulin is an IgG1, an IgG2, an IgG3, or an IgG4. In certain embodiments that may be combined with any of the preceding embodiments, the immunoglobulin comprises an IgG1. In certain embodiments that may be combined with any of the preceding embodiments, the immunoglobulin has a human $C_{H1}$ domain. In certain embodiments that may be combined with any of the preceding embodiments, the immunoglobulin has a human $C_{H2}$ domain. In certain embodiments that may be combined with any of the preceding embodiments, the immunoglobulin has a human $C_{H3}$ domain. In certain embodiments that may be combined with any of the preceding embodiments, the immunoglobulin has a human $C_L$ domain. In certain embodiments that may be combined with any of the preceding embodiments, the immunoglobulin has a binding affinity for a target antigen and the binding affinity for the target antigen is at least seventy percent, at least eighty percent, at least ninety percent, at least one hundred percent, or at least one hundred five percent of the binding affinity of the unmutated immunoglobulin for the target antigen. In certain embodiments that may be combined with the preceding embodiments, the concentrated, liquid solution is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml.

Another aspect includes modified immunoglobulin formulations that can be made up of immunoglobulin of either of the preceding aspects and any and all combinations of the preceding embodiments at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin is at a concentration of greater than the concentration at which the unmutated immunoglobulin aggregates with itself in a concentrated, liquid solution under the same conditions. In certain embodiments that may be combined with the preceding embodiments, at least eighty percent, at least eighty-five percent, at least ninety percent, at least ninety-five percent, at least ninety-six percent, at least ninety-seven percent, at least ninety-eight percent, or at least ninety-nine percent of the modified immunoglobulin is non-aggregated monomer. In certain embodiments that may be combined with any of the preceding embodiments, the formulation includes a pharmaceutically acceptable excipient. In certain embodiments that may be combined with any of the preceding embodiments, the immunoglobulin formulation shows at least five percent, at least ten percent, at least fifteen percent, at least twenty percent, at least twenty-five percent, at least thirty percent, at least thirty-five percent, at least forty percent, or at least fifty percent less aggregate after twenty four hours of accelerated aggregation as compared to the unmutated immunoglobulin under the same conditions. In certain embodiments that may be combined with the preceding embodiments, the aggregation is measured by SEC-HPLC. In certain embodiments that may be combined with any of the preceding embodiments, the immunoglobulin formulation is substantially free of any additive that reduces aggregation of immunoglobulins. In certain embodiments that may be combined with any of the preceding embodiments, the immunoglobulin formulation is substantially free of free histidine, saccharides and polyols.

Yet another aspect includes isolated or recombinant polynucleotides that encode immunoglobulin of either of the preceding modified immunoglobulin aspects and any and all combinations of the preceding embodiments. In certain embodiments, the polynucleotide is in a vector. In certain embodiments, the vector is an expression vector. In certain embodiments that may be combined with the preceding embodiments, an inducible promoter is operably linked to the polynucleotide. Another aspect includes host cells with the vector of either of the preceding embodiments. In certain embodiments, the host cells are capable of expressing the immunoglobulin encoded by the polynucleotide.

Another aspect includes methods of producing an immunoglobulin with a reduced aggregation propensity comprising providing a culture medium comprising the host cell of the preceding aspect and placing the culture medium in conditions under which the immunoglobulin is expressed. In certain embodiments, the methods include an additional step of isolating the immunoglobulin expressed.

Another aspect includes uses of either of the preceding modified immunoglobulin aspects and any and all combinations of the preceding embodiments in the preparation of a medicament comprising a highly concentrated liquid formulation wherein the modified immunoglobulin concentration is at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the use of the medicament is for the treatment of autoimmune diseases, immunological diseases, infectious diseases, inflammatory diseases, neurological diseases, and oncological and neoplastic diseases including cancer. In certain embodiments, the use of the medicament is for the treatment of congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, breast cancer, lung cancer, kidney cancer and rectal cancer; bone metastasis, bone pain management, and humoral malignant hypercalcemia, ankylosing spondylitisa and other spondyloarthropathies; transplantation rejection, viral infections, hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplamacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, and tumors of the vascular system (angiosarcoma and hemangiopericytoma), osteoporosis, hepatitis, HIV, AIDS, spondylarthritis, rheumatoid arthritis, inflammatory bowel diseases (IBD), sepsis and septic shock, Crohn's Disease, psoriasis, schleraderma, graft versus host disease (GVHD), allogenic islet graft rejection, hematologic malignancies, such as multiple myeloma (MM), myelodysplastic syndrome (MDS) and acute myelogenous leukemia (AML), inflammation associated with tumors, peripheral nerve injury or demyelinating diseases. In certain embodiments, the use of the medicament is for the treatment of plaque psoriasis, ulcerative colitis, non-Hodgkin's lymphoma, breast cancer, colorectal cancer, juvenile idiopathic arthritis, macular degeneration, respiratory syncytial virus, Crohn's disease, rheumatoid arthritis, psoriatic arthritis, ankylosing spondylitis, osteoporosis, treatment-induced bone loss, bone metastases, multiple myeloma, Alzheimer's disease, glaucoma, and multiple sclerosis. In certain embodiments that may be combined with any of the preceding embodiments, the use of the medicament further comprises a pharmaceutically acceptable excipient. In certain embodiments that may be combined with any of the preceding embodiments, the immunoglobulin in the medicament shows at least five percent, at least ten percent, at least fifteen percent, at least twenty percent, at least twenty-five percent, at least thirty percent, at least thirty-five percent, at least forty percent, or at least fifty percent less aggregate after twenty four hours of accelerated aggregation as compared to the unmutated immunoglobulin under the same conditions. In certain embodiments, the aggregation is measured by SEC-HPLC. In certain embodiments that may be combined with any of the preceding embodiments, the medicament is substantially free of any additive that reduces aggregation of immunoglobulins. In certain embodiments that may be combined with any of the preceding embodiments, the medicament is substantially free of free histidine, saccharides and polyols.

Another aspect includes uses of either of the preceding modified immunoglobulin aspects and any and all combinations of the preceding embodiments as a non-aggregating pharmaceutical active ingredient.

Another aspect includes pharmaceutical compositions that include an immunoglobulin of either of the preceding aspects and any and all combinations of the preceding embodiments and a pharmaceutically acceptable excipient. In certain embodiments, the immunoglobulin is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin is at a concentration of greater than the concentration at which the unmutated immunoglobulin aggregates with itself in a concentrated, liquid solution under the same conditions. In certain embodiments that may be combined with the preceding embodiments, at least eighty percent, at least eighty-five percent, at least ninety percent, at least ninety-five percent, at least ninety-six percent, at least ninety-seven percent, at least ninety-eight percent, or at least ninety-nine percent of the modified immunoglobulin is non-aggregated monomer. In certain embodiments that may be combined with any of the preceding embodiments, the immunoglobulin formulation shows at least five percent, at least ten percent, at least fifteen percent, at least twenty percent, at least twenty-five percent, at least thirty percent, at least thirty-five percent, at least forty percent, or at least fifty percent less aggregate after twenty four hours of accelerated aggregation as compared to the unmutated immunoglobulin under the same conditions. In certain embodiments that may be combined with the preceding embodiments, the aggregation is measured by SEC-HPLC. In certain embodiments that may be combined with any of the preceding embodiments, the immunoglobulin formulation is substantially free of any additive that reduces aggregation of immunoglobulins. In certain embodiments that may be combined with any of the preceding embodiments, the immunoglobulin formulation is substantially free of free histidine, saccharides and polyols.

Additional aspects and embodiments of the invention may be found throughout the specification.

DETAILED DESCRIPTION OF THE PREFERRED EMBODIMENTS

The present disclosure relates to improved immunoglobulins, particularly human antibodies, that have reduced aggregation. In certain embodiments, the immunoglobulins of the disclosure are modified at specific hydrophobic residues within the constant regions of the heavy or light chains of the immunoglobulin. The disclosure provides modified immunoglobulins, methods of making such immunoglobulins, immunoconjugates and multivalent or multispecific molecules comprising such immunoglobulins and pharmaceutical compositions containing the immunoglobulins, immunoconjugates or bispecific molecules of the disclosure.

DEFINITIONS

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen and at least a portion of the constant region of the heavy or light chain. It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and $C_{H1}$ domains; a F(ab)$_2$ fragment, a bivalent fragment comprising two Fab fragments linked by a disulfide bridge at the hinge region; a Fd fragment consisting of the $V_H$ and $C_{H1}$ domains; and a Fv fragment consisting of the $V_L$ and $V_H$ domains of a single arm of an antibody.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated" antibody or immunoglobulin, as used herein, refers to an antibody or immunoglobulin that is substantially free of other components in which such antibodies or immunoglobulin are naturally found. Moreover, an isolated antibody or immunoglobulin may be substantially free of other cellular material and/or chemicals.

The terms "monoclonal antibody" or "monoclonal antibody composition" as used herein refer to a preparation of antibody molecules of single molecular composition. A monoclonal antibody composition typically displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis as described in Knappik, et al. (2000. J Mol Biol 296, 57-86).

The human antibodies of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human domain", as used herein, is intended to include immunoglobulin constant region domains derived from sequences of human origin, e.g., human germline sequences, or mutated versions of human germline sequences or antibody containing consensus framework sequences derived from human framework sequences analysis as described in Knappik, et al. (2000. J Mol Biol 296, 57-86).

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin comprising a modification as disclosed herein. Due to the replacement with a human constant region, the chimeric antibody can retain its specificity while having reduced antigenicity in human and reduced aggregation overall as compared to the original mouse antibody or a chimeric antibody without the modification as disclosed herein.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The term "Humaneering" as used herein refers to a method for converting non-human antibodies into engineered human antibodies (See e.g., KaloBios' Humaneering™ technology).

As used herein, "isotype" refers to any antibody class (e.g., IgM, IgE, IgG such as IgG1 or IgG2) that is provided by the heavy chain constant region genes that have the aggregation prone motifs disclosed herein (and therefore are amenable to the modifications disclosed herein that reduce aggregation).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. The modifications disclosed herein preferably do not reduce the affinity of the immunoglobulin or antibodies disclosed herein or the affinity is reduced less than thirty percent, less than twenty percent, less than ten percent, or less than five percent. As used herein, when determining whether the modifications disclosed herein reduce affinity the comparison is made between the immunoglobulin or antibody with the modification and the same immunoglobulin lacking the modification but including any unrelated mutations. By way of example, a humanized antibody with an L234K mutation as disclosed herein would be compared to the humanized antibody with the exact same sequence except for the wild type L234.

As used herein, the term "subject" includes any human or nonhuman animal.

The term "nonhuman animal" includes all vertebrates, e.g., mammals and non-mammals, such as nonhuman primates, sheep, dogs, cats, horses, cows, chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. Optimized expression of these sequences in other eukaryotic cells is also envisioned herein. The amino acid sequences encoded by optimized nucleotide sequences are also referred to as optimized.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window", as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BEST-FIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "target antigen" refers to the antigen against which the parent immunoglobulin was raised or otherwise generated (e.g., by phage display).

The term "unmutated immunoglobulin" refers to the immunoglobulin which does not comprise the at least one aggregation reducing mutations. As used herein, the unmutated immunoglobulin may be a hypothetical construct for the purposes of comparison of the aggregation propensity or the binding affinity of the immunoglobulin with and without the aggregation reducing mutations. By way of example, a murine antibody that includes humanizing mutations as well as aggregation reducing mutations is not the unmutated immunoglobulin. The unmutated immunoglobulin would be the antibody with the humanizing mutations, but without the aggregation reducing mutations. Where a mutation is intended to serve more than one purpose including aggregation reduction, the unmutated immunoglobulin does not include such mutation.

The term "aggregation motif" refers to a set of residues grouped together based upon the following process. First, residues having an SAP (5 Å radius) of greater than 0.15 are identified. Then all residues within 5 Å of each residue having an SAP (5 Å radius) of greater than 0.15 are identified. A motif is then the residue with an SAP (5 Å radius) of greater than 0.15 and all residues with an SAP (5 Å radius) of greater than 0.0 within 5 Å of the residue with an SAP (5 Å radius) of greater than 0.15. Any such motifs having at least one residue in common are merged into a larger motif reiteratively until there are no remaining motifs which have a residue in common. These remaining motifs or sets of residues constitute aggregation motifs. Table 2 below sets out the aggregation motifs for the IgG constant domains.

It is accordingly an object of the present invention to provide a modified or isolated immunoglobulin that has a reduced propensity for aggregation comprising at least one aggregation reducing mutation at a residue selected from the group consisting of residues from an aggregation motif 1: 174($C_{H1}$), 175($C_{H1}$), and 181($C_{H1}$); an aggregation motif 2: 226(hinge), 227(hinge), 228(hinge), 229(hinge), 230(hinge), 231(hinge), and 232(hinge); an aggregation motif 3: 234 (hinge) and 235(hinge); an aggregation motif 4: 252($C_{H2}$), and 253($C_{H2}$); an aggregation motif 5: 282($C_{H2}$); an aggregation motif 6: 291($C_{H2}$); an aggregation motif 7: 296($C_{H2}$); an aggregation motif 8: 308($C_{H2}$) and 309($C_{H2}$); an aggregation motif 9: 328($C_{H2}$), 329($C_{H2}$), 330($C_{H2}$), and 331($C_{H2}$); an aggregation motif 10: 395($C_{H3}$), 396($C_{H3}$), 397($C_{H3}$), 398 ($C_{H3}$), and 404($C_{H3}$); an aggregation motif 11: 443($C_{H3}$); an aggregation motif 12: 110($C_L$) and 111($C_L$); an aggregation motif 13: 153($C_L$) and 154($C_L$); and an aggregation motif 14: 201($C_L$), wherein the at least one aggregation reducing mutation is a substitution with an amino acid residue that is less hydrophobic than the residue in the unmodified immunoglobulin and the propensity for aggregation that is reduced is aggregation between immunoglobulin molecules in a concentrated, liquid solution; and wherein the residue numbers are the corresponding Kabat residue numbers in IgG1 based upon alignment with the IgG1 sequence. In certain embodiments, the at least one aggregation reducing mutation residue is selected from the group consisting of residues from an aggregation motif 1: 175($C_{H1}$); an aggregation motif 2: 227 (hinge), 228(hinge), and 230(hinge); an aggregation motif 3: 234(hinge) and 235(hinge); an aggregation motif 4: 253($C_{H2}$); an aggregation motif 5: 282($C_{H2}$); an aggregation motif 6: 291($C_{H2}$); an aggregation motif 7: 296($C_{H2}$); an aggregation motif 8: 309($C_{H2}$); an aggregation motif 9: 329 ($C_{H2}$) and 330($C_{H2}$); an aggregation motif 10: 395($C_{H3}$) and 398($C_{H3}$); an aggregation motif 11: 443($C_{H3}$); an aggregation motif 12: 110($C_L$); an aggregation motif 13: 154($C_L$); and an aggregation motif 14: 201($C_L$). In certain embodiments that may be combined with the preceding embodiments, the aggregation reducing mutation is not residue 234(hinge) or 235(hinge). In certain embodiments that may be combined with the preceding embodiments, the aggregation reducing mutation residue is 234(hinge), 235(hinge), 253($C_{H2}$), or 309 ($C_{H2}$). In certain embodiments that may be combined with the preceding embodiments, the aggregation reducing mutation residue is 253($C_{H2}$) or 309($C_{H2}$). In certain embodiments that may be combined with any of the preceding embodiments, the immunoglobulin has a second aggregation reducing mutation at a hydrophobic residue that (i) has a Spatial-Aggregation-Propensity of at least 0.15, or (ii) is within 5 Å of a residue having a Spatial-Aggregation-Propensity of at least 0.15, wherein the at least one aggregation reducing mutation is a substitution with an amino acid residue that is less hydrophobic than the residue in the unmodified immunoglobulin. In certain embodiments that may be combined with the preceding embodiments having a second aggregation reducing mutation, the aggregation reducing mutation and the second aggregation reducing mutation are at least 5 Å, at least 10 Å, at least 15 Å, or at least 20 Å apart. In certain embodiments that may be combined with any of the preceding embodiments having a second aggregation reducing mutation, the aggregation reducing mutation and the second aggregation reducing mutation are in different aggregation motifs. In certain embodiments that may be combined with any of the preceding embodiments, the immunoglobulin has at least fourteen aggregation reducing mutations wherein each aggregation reducing mutation is selected from a different aggregation motif. In certain embodiments that may be combined with any of the preceding embodiments, the aggregation reducing mutation is substitution with an amino acid residue selected from the group consisting of lysine, arginine, histidine, glutamate, aspartate, glutamine, and asparagine. In certain embodiments that may be combined with any of the preceding embodiments, the aggregation reducing mutation is substitution with an amino acid residue selected from the group consisting of lysine, arginine, and histidine. In certain embodiments that may be combined with any of the preceding embodiments, the aggregation reducing mutation is substitution with a lysine residue. In certain embodiments that may be combined with the preceding embodiments, the Spatial-Aggregation-Propensity (5 Å radius sphere) is calculated using the Black Mould hydrophobicity scale normalized so that glycine equals 0. In certain embodiments that may be combined with any of the preceding embodiments, the immunoglobulin is an IgG1, an IgG2, an IgG3, or an IgG4. In certain embodiments that may be combined with any of the preceding embodiments, the immunoglobulin comprises an IgG1. In certain embodiments that may be combined with any of the preceding embodiments, the immunoglobulin has a human $C_{H1}$ domain. In certain embodiments that may be combined with any of the preceding embodiments, the immunoglobulin has a human $C_{H2}$ domain. In certain embodiments that may be combined with any of the preceding embodiments, the immunoglobulin has a human $C_{H3}$ domain. In certain embodiments that may be combined with any of the preceding embodiments, the immunoglobulin has a human $C_L$ domain. In certain embodiments that may be combined with any of the preceding embodiments, the immunoglobulin has a binding affinity for a target antigen and the binding affinity for the target antigen is at least seventy percent, at least eighty percent, at least ninety percent, at least one hundred percent, or at least one hundred five percent of the binding affinity of the unmutated immunoglobulin for the target antigen. In certain embodiments that may be combined with the preceding embodiments, the concentrated, liquid solution is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml.

It is accordingly a further object of the invention to provide a modified or isolated immunoglobulin that has a reduced propensity for aggregation comprising at least one aggregation reducing mutation at a residue selected from the group consisting of 235(hinge), 241($C_{H2}$), 243($C_{H2}$), 282($C_{H2}$), and 309($C_{H2}$), wherein if residue 235 is selected, it is mutated to a glutamate or a serine, if residue 282 is selected it is mutated to a lysine, and if residue 309 is selected, it is mutated to a lysine, and wherein the at least one aggregation reducing mutation is a substitution with an amino acid residue that is less hydrophobic than the residue in the unmodified immunoglobulin and the propensity for aggregation that is reduced is aggregation between immunoglobulin molecules in a concentrated, liquid solution; and wherein the residue numbers are the corresponding Kabat residue numbers in IgG1 based upon alignment with the IgG1 sequence. In certain embodiments, the at least one aggregation reducing mutation is a mutation of residue 241 to serine, and the modified or isolated immunoglobulin further comprises a second aggregation reducing mutation of residue 243 to serine. In certain embodiments, the at least one aggregation reducing mutation is a mutation of residue 241 to tyrosine, and the modified or isolated immunoglobulin further comprises a second aggregation reducing mutation of residue 243 to tyrosine. In certain embodiments, the at least one aggregation reducing mutation is a mutation of residue 282 to lysine, and the modified or isolated immunoglobulin further comprises a second and a third aggregation reducing mutation, wherein the second aggregation reducing mutation is a mutation of residue 235 to lysine and the third aggregation reducing mutation is a mutation of residue 309 to lysine. In certain embodiments, the immunoglobulin has a second aggregation reducing mutation at a hydrophobic residue, wherein the at least one aggregation reducing mutation is a substitution with an amino acid residue that is less hydrophobic than the residue in the unmodified immunoglobulin. In certain embodiments that may be combined with the preceding embodiments having a second aggregation reducing mutation, the second aggregation reducing mutation (i) has a Spatial-Aggregation-Propensity of at least 0.15, or (ii) is within 5 Å of a residue having a Spatial-Aggregation-Propensity of at least 0.15. In certain embodiments that may be combined with the preceding embodiments having a second aggregation reducing mutation, the immunoglobulin has a third aggregation reducing mutation that (i) has a Spatial-Aggregation-Propensity of at least 0.15, or (ii) is within 5 Å of a residue having a Spatial-Aggregation-Propensity of at least 0.15, wherein the third aggregation reducing mutation is a substitution with an amino acid residue that is less hydrophobic than the residue in the unmodified immunoglobulin. In certain embodiments that may be combined with the preceding embodiments having a second aggregation reducing mutation, the aggregation reducing mutation and the second aggregation reducing mutation are at least 5 Å, at least 10 Å, at least 15 Å, or at least 20 Å apart. In certain embodiments that may be combined with any of the preceding embodiments having a second aggregation reducing mutation, the aggregation reducing mutation and the second aggregation reducing mutation are in different aggregation motifs. In certain embodiments that may be combined with any of the preceding embodiments, the immunoglobulin has at least fourteen aggregation reducing mutations wherein each aggregation reducing mutation is selected from a different aggregation motif. In certain embodiments that may be combined with any of the preceding embodiments, the aggregation reducing mutation is substitution with an amino acid residue selected from the group consisting of lysine, arginine, histidine, glutamate, aspartate, glutamine, asparagine, tyrosine, and serine. In certain embodiments that may be combined with any of the preceding embodiments, the aggregation reducing mutation is substitution with an amino acid residue selected from the group consisting of lysine, serine, glutamate, and histidine. In certain embodiments that may be combined with the preceding embodiments, the Spatial-Aggregation-Propensity (5 Å radius sphere) is calculated using the Black Mould hydrophobicity scale normalized so that glycine equals 0. In certain embodiments that may be combined with any of the preceding embodiments, the immunoglobulin is an IgG1, an IgG2, an IgG3, or an IgG4. In certain embodiments that may be combined with any of the preceding embodiments, the immunoglobulin comprises an IgG1. In certain embodiments that may be combined with any of the preceding embodiments, the immunoglobulin has a human $C_{H1}$ domain. In certain embodiments that may be combined with any of the preceding embodiments, the immunoglobulin has a human $C_{H2}$ domain. In certain embodiments that may be combined with any of the preceding embodiments, the immunoglobulin has a human $C_{H3}$ domain. In certain embodiments that may be combined with any of the preceding embodiments, the immunoglobulin has a human $C_L$ domain. In certain embodiments that may be combined with any of the preceding embodiments, the immunoglobulin has a binding affinity for a target antigen and the binding affinity for the target antigen is at least seventy percent, at least eighty percent, at least ninety percent, at least one hundred percent, or at least one hundred five percent of the binding affinity of the unmutated immunoglobulin for the target antigen. In certain embodiments that may be combined with the preceding embodiments, the concentrated, liquid solution is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml.

Where immunoglobulin residues are referred to by number herein, the residue number refers to the Kabat number of the corresponding residue in the IgG1 molecule when the immunoglobulin sequence of interest is aligned to the human IgG1 immunoglobulin. By way of reference, the human IgG1, IgG2, IgG3 and IgG4 constant domains are aligned:

```
C_H1 domain:
IgG1                                                                    (SEQ ID NO: 1)
IgG2                                                                    (SEQ ID NO: 2)
IgG4                                                                    (SEQ ID NO: 3)
IgG3                                                                    (SEQ ID NO: 4)

..A..     loop    ....B.... loop..C... C'loop..D.
         120         130       140       150       160       170
          |           |         |         |         |         |
    IgG1 ASTKGPSVFPLAPSSKSTSGGTAALGCLVKDYFPEPVTVSWNSGALTSGVHTF
    IgG2 ASTKGPSVFPLAPCSRSTSESTAALGCLVKDYFPEPVTVSWNSGALTSGVHTF
    IgG4 ASTKGPSVFPLAPCSRSTSESTAALGCLVKDYFPEPVTVSWNSGALTSGVHTF
    IgG3 ASTKGPSVFPLAPCSRSTSGGTAALGCLVKDYFPEPVTVSWNSGALTSGVHTF
```

```
          ..  loop  ...E..... loop.  ...F...  loop ..G....join
                   180       190        200       210       220
                    |         |          |         |         |
IgG1  PAVLQSSGLYSLSSVVTVPSSSLGTQTYICNVNHKPSNTKVDKRVEPKSC
IgG2  PAVLWSSGLYSLSSVVTVPSSNFGTQTYTCNVDHKPSNTKVDKTVERKCC
IgG4  PAVLQSSGLYSLSSVVTVPSSSLGTKTYTCNVDHKPSNTKVDKRVESKYG
IgG3  PAVLWSSGLYSLSSVVTVPSSSLGTQTYTCNVNHKPSNTKVDKRVEPKTP
```

Hinge:
IgG1                                                        (SEQ ID NO: 5)
IgG2                                                        (SEQ ID NO: 6)
IgG4                                                        (SEQ ID NO: 7)
IgG3                                                        (SEQ ID NO: 8)

```
            upper                       middle   lower
                                        230
                                         |
IgG1   -DKTHT ---------------- CPPCP APELLGG
IgG2   -VE--- ---------------- CPPCP AP-PVAG
IgG4   -PP--- ---------------- CPSCP APEFLGG
IgG3   LGTTHT CPRCPEPK******** CPRCP APELLGG
```

$C_{H2}$ domain:
IgG1                                                        (SEQ ID NO: 9)
IgG2                                                        (SEQ ID NO: 10)
IgG4                                                        (SEQ ID NO: 11)
IgG3                                                        (SEQ ID NO: 12)

```
         ..A..    loop    ....B....  loop ..C..   C'loop   ...D
          240      240       260      270    280      290
           |        |         |        |      |        |
IgG1  PSVFLFPPKPKDTLMISRTPEVTCVVVDVSHEDPEVKFNWYVDGVEVHNAKTKP
IgG2  PSVFLFPPKPKDTLMISRTPEVTCVVVDVSHEDPEVQFNWYVDGVEVHNAKTKP
IgG4  PSVFLFPPKPKDTLMISRTPEVTCVVVDVSQEDPEVQFNWYVDGVEVHNAKTKP
IgG3  PSVFLFPPKPKDTLMISRTPEVTCVVVDVSHEDPEVQFNWYVDGVEVHNAKTKP ... loop   ....E...  .loop.  ...F.....loop ..G... joinC3
              300       310      320       330      340
               |         |        |         |        |
IgG1  REEQYNSTYRVVSVLTVLHQDWLNGKEYKCKVSNKALPAPIEKTISKAKGQPRE
IgG2  REEQFNSTFRVVSVLTVVHQDWLNGKEYKCKVSNKGLPAPIEKTISKTKGQPRE
IgG4  REEQFNSTYRVVSVLTVLHQDWLNGKEYKCKVSNKGLPSSIEKTISKAKGQPRE
IgG3  REEQYNSTYRVVSVLTVLHQDWLNGKEYKCKVSNKALPAPIEKTISKTKGQPRE
```

$C_{H3}$ domain:
IgG1                                                        (SEQ ID NO: 13)
IgG2                                                        (SEQ ID NO: 14)
IgG4                                                        (SEQ ID NO: 15)
IgG3                                                        (SEQ ID NO: 16)

```
         ..A..    loop    ....B....  loop  ..C...C'loop..D....
          350      360       370      380        390       400
           |        |         |        |          |         |
IgG1  PQVYTLPPSREEMTKNQVSLTCLVKGFYPSDIAVEWESNGQPENNYKTTPPVLDS
IgG2  PQVYTLPPSREEMTKNQVSLTCLVKGFYPSDIAVEWESNGQPENNYKTTPPMLDS
IgG4  PQVYTLPPSQEEMTKNQVSLTCLVKGFYPSDIAVEWESNGQPENNYKTTPPVLDS
IgG3  PQVYTLPPSREEMTKNQVSLTCLVKGFYPSDIAVEWESSGQPENNYKTTPPVLDS loop  ....E...  .loop.  ...F... loop ....G....
                 410        420        430       440
                  |          |          |         |
IgG1  DGSFFLYSKLTVDKSRWQQGNVFSCSVMHEALHNHYTQKSLSLSPGK
IgG2  DGSFFLYSKLTVDKSRWQQGNVFSCSVMHEALHNHYTQKSLSLSPGK
IgG4  DGSFFLYSRLTVDKSRWQEGNVFSCSVMHEALHNHYTQKSLSLSLGK
IgG3  DGSFFLYSKLTVDKSRWQQGNIFSCSVMHEALHNHFTQKSLSLSPGK
```

Spatial-Aggregation-Propensity

The invention herein relates to methods for identifying aggregation prone regions on a protein surface and for preventing or reducing aggregation of a protein. The invention may be applied to generate immunoglobulin with reduced aggregation propensity, i.e., the immunoglobulin in concentrated solution remains primarily in monomeric form rather than higher order aggregated multimers. The methods herein represent an advancement in the ability of computational methods to identify protein regions which may be modified to reduce the propensity of a protein from aggregating. In particular, the methods are based, at least in part, on the calculation of the SAA (Solvent Accessible Area), which is known in the art for characterizing the surface of a protein. SAA gives the surface area of each amino acid or protein structure that is in contact with the solvent. SAA may be typically calculated by computing the locus of the center of a probe sphere as it rolls over the protein surface, i.e., the surface of a protein structural model. The probe sphere has the same radius as that of a water molecule, R=1.4 Å. Alternative methods of calculating SAA, described below, are known in the art and are compatible with the methods described herein.

Although SAA is quite useful to characterize the protein surface, it was not found to be adequate to characterize the hydrophobic patches on the protein surface that are potentially aggregation prone because of the following shortcomings,
1. SAA doesn't distinguish between hydrophobic and hydrophilic regions
2. SAA is not directly proportional to a residue's hydrophobicity (for example, MET has more surface area than LEU but is less hydrophobic)
3. SAA doesn't indicate whether several hydrophobic residues are close-by and thus could enhance the hydrophobicity of a certain region. These residues could be close-by either in primary sequence or in the tertiary structure even though they are far in primary sequence. Either way, they could enhance the hydrophobicity of a certain patch on the antibody surface.

One measure which is described herein, the Effective-SAA, is generated by calculating the hydrophobicity of the fraction of the amino acid which is exposed according to the formula below:

$$\text{Effective-}SAA = \frac{SAA}{SAA_{fully\ exposed}} \times \text{Residue hydrophobicity}$$

A further embodiment of the Effective-SAA further comprises summing the Effective-SAA over at least two, at least three, at least four, at least five or at least six, (e.g., two, three, four, five, six, etc.) amino acid residues which are adjacent in the primary protein sequence. Although the Effective-SAA represents an improvement over the basic SAA, it nevertheless lacks the ability to fully account for the structure of the folded protein and for the fact that amino acids which are not adjacent in the protein sequence may be in proximity to one another in the folded secondary, tertiary, or quaternary structure of a protein. Such protein folds may form aggregation prone regions which do not appear in the primary structure alone, or which may only be detected by more robustly analyzing the folded protein structure.

The present invention provides a new, more advanced measure, called the Spatial-Aggregation-Propensity, which will highlight the effective hydrophobicity of a certain patch or region on the protein surface. The Spatial-Aggregation-Propensity is calculated for defined spatial regions on or near the atoms of a protein structural model.

In this context, a "defined spatial region" is a three-dimensional space or volume chosen to capture a local physical structure and/or chemical environment on or near the protein structure. In a particularly preferred embodiment the Spatial-Aggregation-Propensity is calculated for spherical regions with radius R centered on atoms in a protein (e.g., atoms in a protein structural model). The Spatial-Aggregation-Propensity may also be calculated for spherical regions with radius R centered on chemical bonds, or positioned in space near the structural model. Accordingly, in another embodiment the SAP may be calculated for a defined spatial region centered near an atom, e.g., centered on a point in space which is between 1-10 Å, 1-5 Å, or 1-2 Å from the center of a particular atom or chemical bond.

In certain embodiments, the chosen radius R is between 1 Å and 50 Å. In particular embodiments the chosen radius is at least 1 Å, at least 3 Å, at least 4 Å, at least 5 Å, at least 6 Å, at least 7 Å, at least 8 Å, at least 9 Å, at least 10 Å, at least 11 Å, at least 12 Å, at least 15 Å, at least 20 Å, at least 25 Å, or at least 30 Å. In certain embodiments, the chosen radius is between 5 Å and 15 Å, between 5 Å and 12 Å, or between 5 Å and 10 Å. In specific embodiments the chosen radius is 5 Å or 10 Å.

In other embodiments, the region for which the Spatial-Aggregation-Propensity is calculated is not spherical. The possible shape of the region may further comprise a cube, a cylinder, a cone, an elliptical spheroid, a pyramid, a hemisphere, or any other shape which may be used to enclose a portion of space. In such embodiments, the size of the region may be chosen using measures other than radius, e.g., the distance from the center of the shape to a face or vertex.

In a certain embodiment, the SAP may be used to select residues in a protein, particularly an antibody or immunoglobulin, which may be substituted, thus increasing the protein's stability. In previous studies two main approaches to stabilize a protein in vitro have been to (1) engineer the protein sequence itself and (2) include additives in the liquid formulation. Both approaches have been investigated and significant results have been obtained. The first approach has relied on screening extensive libraries of random variants in silico or experimentally. In the second approach, high-throughput screening for stabilizing additives, as well as rational design of additives permits identification of optimal formulations for a therapeutic protein.

The present invention is expected to streamline the process of stability enhancement by identifying existing hot-spots for aggregation computationally, and analyzing variants with substitutions at those sites experimentally.

Thus, in general terms, a method for calculating the Spatial-Aggregation-Propensity for a particular atom in a protein comprises (a) identifying one or more atoms in a structural model representing the protein, wherein the one or more atoms are within a defined spatial region centered on or near the particular atom; (b) calculating, for each of the one or more atoms in the defined spatial region, a ratio of the solvent accessible area (SAA) of the atoms to the SAA of atoms in an identical residue which is fully exposed; (c) multiplying each ratio by the atom hydrophobicity of the one or more atoms; and (d) summing the products of step (c); whereby the sum is the SAP for the particular atom.

In a related embodiment, the SAP may be calculated according to a different method comprising (a) identifying one or more amino acid residues in a structural model representing the protein, wherein the one or more amino acid residues have at least one atom within a defined spatial region centered on or near the particular atom; (b) calculating, for each of the identified one or more amino acid residues, a ratio of the solvent accessible area (SAA) of atoms in the amino acid to the SAA of atoms in an identical residue which is fully exposed; (c) multiplying each ratio by the hydrophobicity of the one or more amino acid residues as determined by an amino acid hydrophobicity scale; and (d) summing the products of step (c); whereby the sum is the SAP for the particular atom. In preferred embodiments, the structural model is processed prior to step (a) by allowing the structural model to interact with solvent in a molecular dynamics simulation. When an amino acid is identified as having at least one atom within the defined spatial region, the at least one atom may be required to be exclusively an atom in an amino acid side chain. Alternatively it may be an atom required to be a main chain atom.

In other embodiments, this method may further comprise optionally conducting a molecular dynamics simulation prior to step (a) and repeating steps (a)-(d), each time conducting a further molecular dynamics simulation at a plurality of time steps, thereby producing multiple sums as in step (d), and calculating the average of the sums; whereby the calculated average is the SAP for the particular atom.

One of skill in the art will appreciate that an embodiment of the present invention which employs the average of values calculated over a molecular dynamics simulation will be more computationally intensive. Such an embodiment will also, in some cases, provide a more precise or highly resolved map of the Spatial-Aggregation-Propensity. However, experiments discussed herein have shown that the method is still highly accurate when the molecular dynamics averaging is not employed. In one preferred embodiment, Spatial-Aggregation-Propensity values may be calculated for all protein structures in a database, e.g., the Protein Data Bank (PDB), thereby swiftly identifying hydrophobic residues and patches on all known protein structures. This method allows rapid screening of large sets of proteins to identify potential aggregation prone regions and/or protein interaction sites.

In a preferred application, the Spatial-Aggregation-Propensity is described
by the following formula:

$$SAP_{atom} = \Sigma_{Simulation\ Average}(\Sigma_{atoms\ within\ R\ of\ atom} ((SAA\text{-}R/SAA\text{-}fe)*atom\text{-}hb)$$

wherein:
1) SAA-R is SAA of side chain atoms within radius R which is computed at each simulation snapshot. SAA is preferably calculated in the simulation model by computing the locus of the center of a probe sphere as it rolls over the protein surface. The probe sphere has the same radius as that of a water molecule, R=1.4 A. One of skill in the art will appreciate that other methods of computing the SAA would be compatible with the methods described here to calculate SAP. For example, the SAA may be calculated on only amino acid side chain atoms. The SAA may also be calculated on only amino acid main chain atoms (i.e., those atoms of the peptide backbone and associated hydrogens). Alternatively, the SAA may be calculated on only amino acid main chain atoms with the exclusion of associated hydrogens;
2) SAA-fe is SAA of side chain of fully exposed residue (say for amino acid 'X') which is obtained, in a preferred embodiment, by calculating the SAA of side chains of the middle residue in the fully extended conformation of tripeptide 'Ala-X-Ala'; and
3) atom-hb is Atom Hydrophobicity which is obtained as described above using the hydrophobicity scale of Black and Mould (Black and Mould, *Anal. Biochem.* 1991, 193, 72-82). The scale is normalized such that Glycine has a hydrophobicity of zero. Therefore, amino acids that are more hydrophobic than Glycine are positive and less hydrophobic than Glycine are negative on the hydrophobic scale.

A residue which is "fully exposed" is a residue, X, in the fully extended conformation of the tripeptide Ala-X-Ala. One of skill in the art will appreciate that this arrangement is designed such that a calculation of SAA on such a residue, X, will yield the maximum solvent accessible area available. Accordingly, it is contemplated that other residues besides alanine may be used in the calculation without wholly disrupting or altering the results.

As described above, the methods of the present invention may be applied to any protein structural model including an X-ray structure using the same formula as above.

Similarly, if the X-ray structure is not available, the same Spatial-Aggregation-Propensity parameter can be applied to the structure generated through homology modeling, and the SAP parameter may be calculated using the same formula as above.

In certain embodiments the Spatial-Aggregation-Propensity is calculated for all atoms in a protein structural model. In some embodiments, the atomistic Spatial-Aggregation-Propensity values may be averaged over each individual protein residue, or over small groups of residues.

Uses of the SAP Methodology

In one aspect, the present invention may be used as described above to identify hydrophobic amino acid residues, regions or patches in a protein. Without wanting to be held to specific threshold values, atoms or amino acid residues having a Spatial-Aggregation-Propensity >0 are considered to be hydrophobic, or to be in an aggregation prone region. Depending on the type of protein, the particular structure, and the solvent in which it exists, it may be desirable to identify atoms or residues using a cutoff which is slightly below zero, e.g., by choosing atoms or residues which have a Spatial-Aggregation-Propensity of greater than −0.1, −0.15, −0.2, etc. Alternatively, it may be desirable to employ a more stringent cutoff, e.g., 0, 0.05, 0.1, 0.15, 0.2, etc., in order to choose the strongest hydrophobic atoms, residues, or patches. In addition, as the algorithm gives higher numbers to residues at the center of a patch, residues within 3 A, 4 A, 5 A, 7.5 A, or 10 A of the residue meeting the cutoff can also be selected for mutation to less hydrophobic residues to reduce aggregation. In another embodiment, it may be advantageous simply to select atoms or residues having Spatial-Aggregation-Propensity which is larger than atoms or residues which are nearby either sequentially (i.e., along the protein sequence) or, in a preferred embodiment, spatially (i.e., in the three-dimensional structure). One preferred method for selecting atoms or residues in a hydrophobic patch is to map the calculated Spatial-Aggregation-Propensity values, e.g., using a color coding or numerical coding, onto the protein structural model from which they were derived, thus visualizing differences in the Spatial-Aggregation-Propensity across the protein surface and hence allowing easy selection of hydrophobic patches or residues. In a particularly preferred embodiment, the calculations for Spatial-Aggregation-Propensity are carried out separately using two values chosen for the radius, one of higher resolution, e.g., 5 A, and one of lower resolution, e.g., 10 A. In such an embodiment larger or broader hydrophobic patches may be seen on the protein structure with the lower resolution map. Once hydrophobic patches of interest are selected on the low resolution map, those patches may be viewed in greater detail in the higher resolution map which may, in some embodiments, allow one of skill in the art to more easily or more accurately choose residues to mutate or modify. For example, when viewing a hydrophobic patch in the higher resolution map, it may be desirable to select for mutation the residue which has the highest SAP score or is the most hydrophobic (e.g., the most hydrophobic residue in the patch according to the scale of Black and Mould, *Anal. Biochem.* 1991, 193, 72-82).

In a specific embodiment a method to identify an aggregation prone region on a protein comprises (a) mapping onto the structural model the SAP as calculated according to any of the methods described herein for atoms in the protein; and (b) identifying a region within in the protein having a plurality of atoms having a SAP >0; wherein the aggregation prone region comprises the amino acids comprising said plurality of atoms. In such an embodiment the SAP may be calculated for all the atoms in a protein or a portion of the atoms. It is contemplated that one may only calculate the SAP for particular residues or groups of residues which are of interest.

In a similar embodiment, it may be informative to plot the SAP scores of the atoms (or the SAP score as averaged over amino acid residues). Such a plot showing the SAP score along the atoms or residues of a protein allows the easy identification of peaks, which may indicate candidates for replacement. In a particularly preferred embodiment the SAP scores along the atoms or residues in the protein are plotted in a graph and the Area Under the Curve (AUC) is calculated for peaks in the graph. In such an embodiment, peaks with a larger AUC represent larger or more hydrophobic aggregation prone regions. In particular embodiments it will be desirable to select for replacement one or more residues which are identified as existing in a peak, or, more preferably, in a peak with a large AUC.

In particular embodiments the present invention may be used to make an immunoglobulin variant which exhibits a reduced propensity for aggregation by replacing at least one amino acid residue within an aggregation prone region in the immunoglobulin identified by any of the methods described herein with an amino acid residue which is more hydrophilic then the residue which is being replaced, such that the propensity for aggregation of the variant is reduced. As used herein, when amino acid residues are referred to as "more" or "less" hydrophilic or hydrophobic, it will be appreciated by the skilled artisan that this signifies more or less hydrophobic as compared to another amino acid according to a measure of hydrophobicity (hydrophilicity) known in the art, e.g., the hydrophobicity scale of Black and Mould.

In a similar embodiment the present invention may be used to make an immunoglobulin variant which exhibits a reduced propensity for aggregation by generating a plurality of immunoglobulin variants by replacing, in each variant at least one residue within an aggregation prone region in the immunoglobulin, wherein the aggregation prone region is identified using SAP scores calculated according any method described herein, wherein one or different residues, or different combinations of residues are replaced in each variant, and wherein the at least one residue is replaced with a residue which is more hydrophilic; and (b) selecting an immunoglobulin variant prepared as in (a) which exhibits a reduced propensity for aggregation.

In addition, an amino acid residue in an aggregation prone region may be deleted rather than replaced. In some immunoglobulins where multiple amino acid residues are selected for replacement, some residues may be replaced while others are deleted.

In further embodiments multiple aggregation prone regions or residues may be identified in an initial immunoglobulin by the methods described above (e.g., by using a Spatial-Aggregation-Propensity cutoff above which residues are selected). Subsequently, a plurality of immunoglobulin variants may be generated by replacing in said initial immunoglobulin one or more selected amino acid residues (or one or more residues falling in selected patch) with amino acid residues which are more hydrophilic, such that a plurality of immunoglobulin variants are created representing a variety of different amino acid substitutions. This population may then be screened to select one or more immunoglobulin variants which have a reduced propensity for aggregation. One of skill in the art will appreciate that multiple aggregation prone regions may be identified, and that one or more substitutions and/or deletions may be made in one or more aggregation prone regions. The relative hydrophobicity of the amino acids may be determined by the hydrophobicity scale of Black and Mould as described above. In specific embodiments, an amino acid to be replaced is selected from the group comprising or consisting of Phe, Leu, Ile, Tyr, Trp, Val, Met, Pro, Cys, Ala, or Gly. In related embodiments, the more hydrophilic amino acid which will be substituted into the immunoglobulin will be chosen from the group comprising or consisting of Thr, Ser, Lys, Gln, Asn, His, Glu, Asp, and Arg.

It is accordingly an object of the present invention to provide modified and/or isolated immunoglobulins that have a reduced propensity for aggregation comprising at least one aggregation reducing mutation at a residue in a conserved domain of the immunoglobulin that (i) has a Spatial-Aggregation-Propensity (5 Å radius sphere) of at least 0.15, or (ii) has an Spatial-Aggregation-Propensity (5 Å radius sphere) of greater than 0.0 and is within 5 Å of a residue having a Spatial-Aggregation-Propensity (5 Å radius sphere) of at least 0.15, wherein the at least one aggregation reducing mutation is a substitution with an amino acid residue that lowers the Spatial-Aggregation-Propensity (5 Å radius sphere) of the residue as compared to the unmutated immunoglobulin and the propensity for aggregation that is reduced is aggregation between immunoglobulin molecules in a concentrated, liquid solution. In certain embodiments, the at least one aggregation reducing mutation is not at a residue corresponding to Kabat residue 234(hinge) or 235(hinge) in IgG1 based upon alignment with the IgG1 sequence. In certain embodiments that may be combined with the preceding embodiments, the immunoglobulin has a second aggregation reducing mutation at a residue that (i) has a Spatial-Aggregation-Propensity (5 Å radius sphere) of at least 0.15, or (ii) has an Spatial-Aggregation-Propensity (5 Å radius sphere) of greater than 0.0 and is within 5 Å of a residue having a Spatial-Aggregation-Propensity (5 Å radius sphere) of at least 0.15, wherein the second aggregation reducing mutation is a substitution with an amino acid residue that is a substitution with an amino acid residue that lowers the Spatial-Aggregation-Propensity (5 Å radius sphere) of the residue as compared to the unmutated immunoglobulin. In certain embodiments that may be combined with the preceding embodiments having a second aggregation reducing mutation, the aggregation reducing mutation and the second aggregation reducing mutation are at least 5 Å, at least 10 Å, at least 15 Å, or at least 20 Å apart. In certain embodiments that may be combined with the preceding embodiments having a second aggregation reducing mutation, the aggregation reducing mutation and the second aggregation reducing mutation are in different aggregation motifs. In certain embodiments that may be combined with any of the preceding embodiments, the aggregation reducing mutation is a substitution with an amino acid residue that is less hydrophobic than the residue in the unmodified immunoglobulin. In certain embodiments that may be combined with the preceding embodiments, the aggregation reducing mutation is a substitution with an amino acid residue selected from the group consisting of lysine, arginine, histidine, glutamate, aspartate, glutamine, and asparagine. In certain embodiments that may be combined with the preceding embodiments, the aggregation reducing mutation is a substitution with an amino acid residue selected from the group consisting of lysine, arginine, and histidine. In certain embodiments that may be combined with the preceding embodiments, the aggregation reducing mutation is a substitution with a lysine residue. In certain embodiments that may be combined with the preceding embodiments, the Spatial-Aggregation-Propensity (5 Å radius sphere) is calculated using the Black Mould hydrophobicity scale normalized so that glycine equals 0. In certain embodiments that may be combined with the preceding embodiments, the immunoglobulin is an IgG1, an IgG2, an IgG3, or an IgG4. In certain embodiments that may be combined with the preceding embodiments, the immunoglobulin is an IgG1. In certain embodiments that may be combined with the preceding embodiments, the immunoglobulin has a human $C_{H1}$ domain. In certain embodiments that may be combined with the preceding embodiments, the immunoglobulin has a human $C_{H2}$ domain. In certain embodiments that may be combined with the preceding embodiments, the immunoglobulin has a human $C_{H3}$ domain. In certain embodiments that may be combined with the preceding embodiments, the immunoglobulin has a human $C_L$ domain. In certain embodiments that may be combined with the preceding embodiments, the immunoglobulin has a binding affinity for a target antigen and the binding affinity for the target antigen is at least seventy percent, at least eighty percent, at least ninety percent, at least one hundred percent, or at least one hundred five percent of the binding affinity of the unmutated immunoglobulin for the target antigen. In certain embodiments that may be combined with the preceding embodiments, the concentrated, liquid solution is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml.

Immunoglobulin variants may be made by any method known in the art including site directed mutagenesis and other recombinant DNA technology, e.g., see U.S. Pat. Nos. 5,284, 760; 5,556,747; 5,789,166; 6,878,531; 5,932,419; and, 6391548.

In particular embodiments the present invention may be used to make an immunoglobulin variant which exhibits a reduced propensity for aggregation by replacing at least one amino acid residue within an aggregation prone region in the immunoglobulin identified by any of the methods described herein with a natural amino acid residue, a modified amino acid residue, an unusual amino acid residue, an unnatural amino acid residue, or an amino acid analog or derivative which is more hydrophilic then the residue which is being replaced, such that the propensity for aggregation of the variant is reduced.

The synthesis of unnatural amino acids is known to those of skill in the art, and is further described, e.g., in U.S. Patent Publication No. 2003-0082575. In general, any method known in the art to synthesize or incorporate unnatural, modified, or unusual amino acids into proteins may be employed including, but not limited to those methods described or referenced in the publications Liao J. *Biotechnol Prog.* 2007 January-February; 23(1):28-31; Rajesh, and Iqbal. *Curr Pharm Biotechnol.* 2006 August; 7(4):247-59; Cardillo et al. *Mini Rev Med. Chem.* 2006 March; 6(3):293-304; Wang et al. *Annu Rev Biophys Biomol Struct.* 2006; 35:225-49; Chakraborty et al., *Glycoconj J.* 2005 March; 22(3):83-93. As a further example, the Ambrx ReCODE™ technology may be employed to develop and incorporate unnatural amino acids, or unusual amino acids into proteins as indicated by the methods described herein.

Immunoglobulin variants according to the invention can exhibit enhanced or improved stability as determined, for example, by accelerated stability studies. Exemplary accelerated stability studies include, but are not limited to, studies featuring increased storage temperatures. A decrease in the formation of aggregates observed for a immunoglobulin variant as compared to the wild type or initial protein indicates an increased stability. Stability of immunoglobulin variants may also be tested by measuring the change in the melting temperature transition of a variant as compared to the wild type or initial immunoglobulin. In such an embodiment, increased stability would be evident as an increase in the melting temperature transition in the variant. Additional methods for measuring protein aggregation are described in U.S. patent application Ser. No. 10/176,809.

It is accordingly an object of the present invention to provide isolated or recombinant polynucleotides that encode modified immunoglobulins as discussed in paragraphs [0059], [0060], or [0089] and any and all combinations of their embodiments. In certain embodiments, the polynucleotide is in a vector. In certain embodiments, the vector is an expression vector. In certain embodiments that may be combined with the preceding embodiments, an inducible promoter is operably linked to the polynucleotide. Another aspect includes host cells with the vector of either of the preceding embodiments. In certain embodiments, the host cells are capable of expressing the immunoglobulin encoded by the polynucleotide.

It is accordingly an object of the present invention to provide methods of producing an immunoglobulin with a reduced aggregation propensity comprising providing a culture medium comprising the host cell of the preceding paragraph and placing the culture medium in conditions under which the immunoglobulin is expressed. In certain embodiments, the methods include an additional step of isolating the immunoglobulin expressed.

In another aspect of the invention the calculated Spatial-Aggregation-Propensity may be used to identify protein-protein interaction sites on the surface of a protein structure. It is known in the art that protein interaction sites often contain hydrophobic residues or hydrophobic patches. It is expected that the methods described herein will be useful in locating binding sites by identifying hydrophobic patches. Such hydrophobic patches will then be candidates for protein-protein or protein-ligand recognition sites.

In some embodiments, the invention further relates to computer code for determining SAP according to the methods of the invention. In other embodiments, the invention relates to a computer, a supercomputer, or cluster of computers dedicated to performing the methods of the invention. In yet other aspect, the invention provides a web-based, server based, or internet based service for determining aggregation prone regions on a protein, the service comprising accepting data about a protein (e.g., a protein structural model) from a user (e.g., over the internet) or retrieving such data from a database such that the service provider can generate, retrieve, or access a static structure of the protein, optionally including molecular dynamics modeling of the protein to provide a dynamic structure of the protein, determining SAP for atoms or residues of the protein based on the static or dynamic structure so generated, and returning the SAP data, for example, as a structural model mapped with said SAP data by the service provider, to a user. In some embodiments, the user is a person. In other embodiments the user is a computer system or automated computer algorithm.

In some embodiments the present invention proves an SAP calculation system comprising: a web server for providing a web service for calculating SAP to a user terminal through the Internet; a database for storing general information on the calculation method, amino acid hydrophobicity, etc., and a calculation server for performing the SAP calculation based on information in the database and information provided or transmitted through the internet by the user.

In some embodiments, the web server and the calculation server are the same computer system. In some embodiments the computer system is a supercomputer, a cluster computer, or a single workstation or server. In a related embodiment the web server of the SAP calculation system further comprises a controller for controlling the entire operation, a network connection unit for connection to the Internet, and a web service unit for providing a web service for calculating SAP to the user terminal connected through the Internet.

In addition, embodiments of the present invention further relate to computer storage products with a computer readable medium that contain program code for performing various computer-implemented operations, e.g., calculating the SAP for a structural model, calculating SAA, calculating effective-SAA, manipulating structural models, implementing molecular dynamics simulations, organizing and storing relevant data, or performing other operations described herein. The computer-readable medium is any data storage device that can store data which can thereafter be read by a computer system. Examples of computer-readable media include, but are not limited to hard disks, floppy disks, flash drives, optical discs (e.g., CDs, DVDs, HD-DVDs, Blu-Ray discs, etc.) and specially configured hardware devices such as application specific integrated circuits (ASICs) or programmable logic devices (PLDs). The computer-readable medium can also be distributed as a data signal embodied in a carrier wave over a network of coupled computer systems so that the computer readable code is stored and executed in a distributed fashion. It will be appreciated by those skilled in the art that the above described hardware and software elements are of standard design and construction. The computer, internet, server, and service related embodiments described above may further apply to the SAA and the effective-SAA as well as SAP.

Pharmaceutical Compositions Containing Immunoglobulins and Immunogobulin Variants In another aspect, the present invention provides a composition, e.g., a pharmaceutical composition, containing one or more immunoglobulin variants produced by the methods of the invention, formulated together with a pharmaceutically acceptable carrier. Pharmaceutical compositions of the invention also can be administered in combination therapy, i.e., combined with other agents. For example, the combination therapy can include an immunoglobulin of the present invention combined with at least one other anti-cancer agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the immunoglobulin or variant thereof of the invention, may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Exemplary formulations comprise at least one immunoglobulin variant of the invention and can comprise lower concentrations of stabilizing (or disaggregation) agents which can, in addition to the methods disclosed herein, be used to prevent or diminish aggregation of an immunoglobulin. Accordingly, conventional methods used to prevent aggregation may be employed in the development of pharmaceutical compositions containing immunoglobulin variants produced by the methods of the present invention. For example, a variety of stabilizing or disaggregating compounds may be included in pharmaceutical compositions of the invention depending on their intended use and their biological toxicity. Such stabilizing compounds may include, for example, cyclodextrin and its derivatives (U.S. Pat. No. 5,730,969), alkylglycoside compositions (U.S. patent application Ser. No. 11/474,049), the use of chaperone molecules (e.g., LEA (Goyal et al., *Biochem J.* 2005, 388(Pt 1):151-7; the methods of U.S. Pat. No. 5,688,651), betaine compounds (Xiao, Burn, Tolbert, *Bioconjug Chem.* 2008 May 23), surfactants (e.g., Pluronic F127, Pluronic F68, Tween 20 (Wei et al. *Interna-*

*tional Journal of Pharmaceutics.* 2007, 338(1-2):125-132)), and the methods described in U.S. Pat. Nos. 5,696,090, 5,688,651, and 6,420,122.

In addition, proteins, and in particular antibodies, are stabilized in formulations using combinations of different classes of excipients, e.g., (1) disaccharides (e.g. Saccharose, Trehalose) or polyols (e.g. Sorbitol, Mannitol) act as stabilizers by preferential exclusion and are also able to act as cryoprotectants during lyophilization, (2) surfactants (e.g. Polysorbat 80, Polysorbat 20) act by minimizing interactions of proteins on interfaces like liquid/ice, liquid/material-surface and/or liquid/air interfaces and (3) buffers (e.g. phosphate-, citrate-, histidine) help to control and maintain formulation pH. Accordingly, such disaccharides polyols, surfactants and buffers may be used in addition to the methods of the present invention to further stabilize immunoglobulins and prevent their aggregation.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

It is accordingly an object of the present invention to provide modified immunoglobulin formulations that can be made up of modified immunoglobulins as discussed in paragraphs [0059], [0060], or [0089] and any and all combinations of their embodiments at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin is at a concentration of greater than the concentration at which the unmutated immunoglobulin aggregates with itself in a concentrated, liquid solution under the same conditions. In certain embodiments that may be combined with the preceding embodiments, at least eighty percent, at least eighty-five percent, at least ninety percent, at least ninety-five percent, at least ninety-six percent, at least ninety-seven percent, at least ninety-eight percent, or at least ninety-nine percent of the modified immunoglobulin is non-aggregated monomer. In certain embodiments that may be combined with any of the preceding embodiments, the formulation includes a pharmaceutically acceptable excipient. In certain embodiments that may be combined with any of the preceding embodiments, the immunoglobulin formulation shows at least five percent, at least ten percent, at least fifteen percent, at least twenty percent, at least twenty-five percent, at least thirty percent, at least thirty-five percent, at least forty percent, or at least fifty percent less aggregate after twenty four hours of accelerated aggregation as compared to the unmutated immunoglobulin under the same conditions. In certain embodiments that may be combined with the preceding embodiments, the aggregation is measured by SEC-HPLC. In certain embodiments that may be combined with any of the preceding embodiments, the immunoglobulin formulation is substantially free of any additive that reduces aggregation of immunoglobulins. In certain embodiments that may be combined with any of the preceding embodiments, the immunoglobulin formulation is substantially free of free histidine, saccharides and polyols.

It is accordingly an object of the present invention to provide uses of the modified immunoglobulins of the present disclosure and any and all combinations of their embodiments as a non-aggregating pharmaceutical active ingredient.

It is accordingly an object of the present invention to provide pharmaceutical compositions that include a modified immunoglobulin of the present disclosure and any and all combinations of their embodiments and a pharmaceutically acceptable excipient. In certain embodiments, the immunoglobulin is at a concentration of at least 10 mg/ml, at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the immunoglobulin is at a concentration of greater than the concentration at which the unmutated immunoglobulin aggregates with itself in a concentrated, liquid solution under the same conditions. In certain embodiments that may be combined with the preceding embodiments, at least eighty percent, at least eighty-five percent, at least ninety percent, at least ninety-five percent, at least ninety-six percent, at least ninety-seven percent, at least ninety-eight percent, or at least ninety-nine percent of the modified immunoglobulin is non-aggregated monomer. In certain embodiments that may be combined with any of the preceding embodiments, the immunoglobulin formulation shows at least five percent, at least ten percent, at least fifteen percent, at least twenty percent, at least twenty-five percent, at least thirty percent, at least thirty-five percent, at least forty percent, or at least fifty percent less aggregate after twenty four hours of accelerated aggregation as compared to the unmutated immunoglobulin under the same conditions. In certain embodiments that may be combined with the preceding embodiments, the aggregation is measured by SEC-HPLC. In certain embodiments that may be combined with any of the preceding embodiments, the immunoglobulin formulation is substantially free of any additive that reduces aggregation of immunoglobulins. In certain embodiments that may be combined with any of the preceding embodiments, the immunoglobulin formulation is substantially free of free histidine, saccharides and polyols.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the immunoglobulin, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an immunoglobulin of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively an immunoglobulin of the invention can be administered as a sustained release formulation, in which case less frequent administration is required. Dosage and frequency vary depending on the half-life of the administered substance in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of immunoglobulin of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for binding moieties of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an immunoglobulin of the invention can be administered via a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824;

or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

It is accordingly an object of the present invention to provide methods for reducing the aggregation propensity of an immunoglobulin in a highly concentrated pharmaceutical formulation comprising providing an immunoglobulin that is prone to aggregation; substituting a residue in a conserved domain of the immunoglobulin that (i) has a Spatial-Aggregation-Propensity of at least 0.15, or (ii) has an Spatial-Aggregation-Propensity (5 Å radius sphere) of greater than 0.0 and is within 5 Å of a residue having a Spatial-Aggregation-Propensity of at least 0.15, with an amino acid residue that lowers the Spatial-Aggregation-Propensity (5 Å radius sphere), and generating a highly concentrated, liquid formulation of the modified immunoglobulin wherein the modified immunoglobulin concentration is at least 20 mg/ml, at least 30 mg/ml, at least 40 mg/ml, at least 50 mg/ml, at least 75 mg/ml, at least 100 mg/ml, at least 125 mg/ml, or at least 150 mg/ml, and wherein the aggregation propensity that is reduced is aggregation between immunoglobulin molecules in a concentrated, liquid solution.

It is accordingly an object of the present invention to provide uses of the modified immunoglobulins as discussed in paragraphs [0059], [0060], or [0089] and any and all combinations of their embodiments in the preparation of a medicament comprising a highly concentrated liquid formulation wherein the modified immunoglobulin concentration is at least 20 mg/ml, at least 30 mg/ml, at least 40 mg/ml, at least 50 mg/ml, at least 75 mg/ml, at least 100 mg/ml, at least 125 mg/ml, or at least 150 mg/ml. In certain embodiments, the use of the medicament is for the treatment of autoimmune diseases, immunological diseases, infectious diseases, inflammatory diseases, neurological diseases, and oncological and neoplastic diseases including cancer. In certain embodiments, the use of the medicament is for the treatment of congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, breast cancer, lung cancer, kidney cancer and rectal cancer; bone metastasis, bone pain management, and humoral malignant hypercalcemia, ankylosing spondylitisa and other spondyloarthropathies; transplantation rejection, viral infections, hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplamacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, and tumors of the vascular system (angiosarcoma and hemangiopericytoma), osteoporosis, hepatitis, HIV, AIDS, spondylarthritis, rheumatoid arthritis, inflammatory bowel diseases (IBD), sepsis and septic shock, Crohn's Disease, psoriasis, schleraderma, graft versus host disease (GVHD), allogenic islet graft rejection, hematologic malignancies, such as multiple myeloma (MM), myelodysplastic syndrome (MDS) and acute myelogenous leukemia (AML), inflammation associated with tumors, peripheral nerve injury or demyelinating diseases. In certain embodiments, the use of the medicament is for the treatment of plaque psoriasis, ulcerative colitis, non-Hodgkin's lymphoma, breast cancer, colorectal cancer, juvenile idiopathic arthritis, macular degeneration, respiratory syncytial virus, Crohn's disease, rheumatoid arthritis, psoriatic arthritis, ankylosing spondylitis, osteoporosis, treatment-induced bone loss, bone metastases, multiple myeloma, Alzheimer's disease, glaucoma, and multiple sclerosis. In certain embodiments that may be combined with any of the preceding embodiments, the use of the medicament further comprises a pharmaceutically acceptable excipient. In certain embodiments that may be combined with any of the preceding embodiments, the immunoglobulin in the medicament shows at least five percent, at least ten percent, at least fifteen percent, at least twenty percent, at least twenty-five percent, at least thirty percent, at least thirty-five percent, at least forty percent, or at least fifty percent less aggregate after twenty four hours of accelerated aggregation as compared to the unmutated immunoglobulin under the same conditions. In certain embodiments, the aggregation is measured by SEC-HPLC. In certain embodiments that may be combined with any of the preceding embodiments, the medicament is substantially free of any additive that reduces aggregation of immunoglobulins. In certain embodiments that may be combined with any of the preceding embodiments, the medicament is substantially free of free histidine, saccharides and polyols.

EXAMPLES

Molecular simulation techniques for predicting aggregation prone regions and studying the mechanism of aggregation have mostly employed comparatively simple simulation models (Ma and Nussinov. *Curr. Opin. Chem. Biol.* 2006, 10, 445-452; Cellmer, et al., *TRENDS in Biotechnology* 2007, 25(6), 254) unlike the detailed atomistic models which may be employed in the present invention. The least detailed of the simulation models employed was the lattice model, which was used in numerous studies of protein aggregation (Harrison et al. *J. MoL Biol.* 1999, 286, 593-606; Dima and Thirumalai. *Protein Sci.* 2002, 11, 1036-1049; Leonhard et al. *Protein Sci.* 2004, 13, 358-369; Patro and Przybycien. *Biophys. J.* 1994, 66, 1274-1289; Patro and Przybycien. *Biophys. J.* 1996, 70, 2888-2902; Broglia et al. *Proc. Natl. Acad. Sci. U.S.A.* 1998, 95, 12930-12933; Istrail et al. *Comput. Biol.* 1999, 6, 143-162; Giugliarelli et al. *Chem. Phys.* 2000, 113, 5072-5077; Bratko et al. *J. Chem. Phys.* 2001, 114, 561-569; Bratko and Blanch *J. Chem. Phys.* 2003, 118, 5185-5194; Combe and Frenkel *Chem. Phys.* 2003, 118, 9015-9022; Toma and Toma. *Biomacromolecules* 2000, 1, 232-238; Gupta et al. *Protein Sci.* 1998, 7, 2642-2652; and Nguyen and Hall *Biotechnol. Bioeng.* 2002, 80, 823-834). Here each residue is represented as a bead occupying a single site on a three dimensional lattice. Because of its simplicity, the lattice model is less computationally demanding and has been used to simulate large systems for long time scales. Although these lattice models provide insight into the basic physics underlying protein aggregation, they do not accurately represent the secondary and tertiary structure, and cannot adequately account for different atomistic level interactions such as hydrogen bonding.

A more detailed model compared to the lattice model is the intermediate resolution model in which a few atoms are usually combined into a single bead, and pseudo-bonds are sometimes introduced to maintain the backbone bond angles and isomerization states (Smith and Hall, *Mol. Biol.* 2001, 312, 187-202; Smith and Hall. *Proteins: Struct., Funct., Genet.* 2001, 44, 344-360; Smith and Hall. *Proteins: Struct., Funct., Genet.* 2001, 44, 376-391; Nguyen, et al., *Protein Sci.* 2004, 13, 2909-2924; Nguyen and Hall, *Proc. Natl. Acad. Sci. U.S.A.*, 2004, 101(46), 16180-16185; Nguyen and Hall. *J. Am. Chem. Soc.*, 2006, 128, 1890-1901; Jang, et al., *Biophys. J.* 2004, 86, 31-49; Jang, et al., *Protein Sci.* 2004, 13, 40-53). This model was successfully used to simulate the formation of fibrils from systems containing between 12 and 96 polyalanine peptides (16-residue each) starting from a random state (Nguyen and Hall, *Proc. Natl. Acad. Sci. U.S.A.*, 2004, 101(46), 16180-16185; Nguyen and Hall, *J. Am. Chem. Soc.*, 2006, 128, 1890-1901). Dokholyan and co-workers applied such a model to study the formation of fibrillar β-sheet structures by eight model Src SH3 domain proteins (Ding, et al., *Mol. Biol.* 2002, 324, 851-857) or by 28 model A β (1-40) peptides (Peng, et al., *Phys. Rev. E: Stat. Ph. Interdiscip. Top.* 2004, 69, 41908-41914.).

Unlike simpler models, atomistic models include all the atomistic details such as hydrogen bonding and are thus more accurate than the lattice or the intermediate resolution models. Such atomistic models have been used either with an explicit solvent, or with an implicit solvent where the solvent is treated as a continuum. The explicit model is more accurate than the implicit model, but is also more computationally demanding. Such an atomistic model with implicit solvent was used to study the early stages of aggregation of the heptapeptide GNNQQNY (SEQ ID NO: 17), which is a part of the yeast protein Sup35 (Gsponer, et al., *Proc. Natl. Acad. Sci. U.S.A.* 2003, 100, 5154-5159.). A similar model was used for the aggregation of Ab16-22 amyloid peptide (KLVFFAE (SEQ ID NO: 18)) into antiparallel β Sheets (Klimov and Thirumalai, *Structure* 2003, 11, 295-307). Dokholyan and coworkers (Khare, et al., *Proteins.* 2005, 61, 617-632.) used an explicit atomistic model to investigate the ordered aggregation propensity along the sequence of the enzyme Cu, Zn superoxide dismutase (SOD1). They have decomposed the SOD1 sequence into overlapping heptapeptides and performed a large number of explicit water molecular dynamics simulations (each of 0.5 ns) of monomeric, dimeric and tetrameric segments. With this they identified the amyloidogenic regions in the SOD1 sequence to be: the two termini, the β-strands 4 and 7, and the two crossover loops.

A similar molecular dynamics simulation protocol was developed to obtain structural information on ordered β-aggregation of amyloidogenic polypeptides (Cecchini et al., *J Mol. Biol.* 2006, 357, 1306-1321.). The procedure is based on the decomposition of a polypeptide chain into overlapping segments and equilibrium molecular dynamics (MD) simulations of a small number of copies of each segment. The β-aggregation propensity along the sequence of the Alzheimer's Aβ (1-42) peptide was found to be highly heterogeneous with a maximum at the segment $V_{12}$HHQKLVFFAE$_{22}$ (SEQ ID NO: 19) and minima at four turn-like dipeptides. Using this technique, the predicted change in the aggregation propensity of a double-point mutant of the N-terminal domain of the yeast prion Ure2p was verified in vitro using the thioflavin T binding assay. Such a procedure to decompose the polypeptide chain into overlapping segments would be extremely challenging for systems such as antibodies because of their huge size. Even an atomistic simulation of a single full antibody in explicit solvent is very computationally demanding because of the huge size of an antibody. Therefore, there does not appear to be full antibody atomistic simulation in the literature.

However, there have been atomistic simulations of small parts of the antibody, mostly for the Fab fragment (Noon, et al., *PNAS.* 2002, 99, 6466; Sinha and Smith-Gill, *Cell Biochemistry and Biophysics.* 2005, 43, 253). In the work disclosed herein, atomistic simulations of a full antibody molecule with an explicit solvent were performed. Based on these simulations, the aggregation prone regions on the antibody were identified using the 'Spatial-Aggregation-Propensity' parameter described herein. These aggregation prone regions were then mutated to design antibodies with enhanced stability. The Examples described herein refer to particular, non-limiting embodiments of the invention.

Example 1

Molecular Dynamics Simulation Methodology

Molecular dynamics simulations were performed for a full antibody using an all atom model. The initial structure for simulation for the full antibody was obtained from the X-ray structures of individual Fab and Fc fragments. The X-ray structure of a proof-of-concept (POC) Fab fragment was selected for modeling onto the X-ray structure of Fc obtained from the IgG1 antibody 1HZH (Saphire et al., *Science.* 2001, 93, 1155). 1HZH was chosen since the X-ray structure is known for the full antibody and since the Fc structure is the same for all of the IgG1 class of antibodies. The structure of a full POC antibody was then obtained by aligning the Fab and Fc fragments using the 1HZH structure as a model template. In order to align the fragments at the correct distance and orientation, the RMSD (Root Mean Square Deviation) was minimized between the common CYS residues of the fragments and the full antibody template (1HZH). The CYS residues were chosen because each antibody sub-domain ($C_{H1}$, $C_{H2}$ etc.) contains a disulphide bond, and thus CYS residues are broadly distributed across the whole antibody structure. The resulting full antibody structure was then used to perform explicit atom simulations for 30 ns. A G0 glycosylation pattern was used for the simulations since this is the most common glycosylation pattern observed in antibodies.

The CHARMM simulation package (Brooks et al. *J. Comput. Chem.,* 1983, 4, 187) was used for set-up and analysis, and the NAMD package (Phillips et al. *Journal of Computa-* tional Chemistry. 2005, 26, 1781) for performing simulations. The CHARMM fully atomistic force field (MacKerell et al. *J. Phys Chem. B.* 1998, 102, 3586) was used for the protein and TIP3P (Jorgensen et al. J. Chem. Phys., 1983, 79, 926) solvent model for water. The simulations were performed at 298K and 1atm in the NPT ensemble. The parameters for the sugar groups involved in glycosylation of the Fc fragment were derived to be consistent with the CHARMM force field, following from the CSFF force field (Kuttel et al. *J. Comput. Chem.,* 2002, 23, 1236). The protonation states of Histidine residues at pH-7 were chosen based on the spatial proximity of electro-negative groups. The full antibody was solvated in an orthorhombic box since this minimizes the number of water molecules required and thus minimizes the computational time. Periodic boundary conditions were used in all 3 directions. A water solvation shell of 8 Å was used in each direction of the orthorhombic box. The resulting total system size was 202130 atoms. Sufficient ions were added to neutralize the total charge of the system. The charge neutrality is required by the Ewald summation technique employed to calculate the contribution of electrostatic interactions in the system.

After the antibody was solvated, the energy was initially minimized with SD (Steepest Descents) by fixing the protein to allow the water to relax around the protein. Then the restraints were removed and the structure was further minimized with SD and ABNR (Adopted Basis Newton-Raphson). The system was then slowly heated to room temperature with 5° C. increment every 0.5 ps using a 1fs time step. The system was then equilibrated for 1ns before computing properties of interest from the simulation. The configurations were saved every 0.1 ps during the simulation for further statistical analysis.

Example 2

Calculation of the Spatial Aggregation Propensity (SAP)

In order to overcome the shortcomings of SAA, a new parameter was defined called 'Spatial-Aggregation-Propensity' as described above.

In this example the 'Spatial-Aggregation-Propensity' was calculated for spherical regions with radius R centered on every atom in the antibody described in Example 1. The value of Spatial-Aggregation-Propensity was thus evaluated with a 30 ns simulation average for the Fc-fragment of the antibody for two different radii of patches (R=5 Å, 10 Å) (One of skill in the art will appreciate various time steps for simulation may be chosen according to the computational resources available and the desired resolution of the result). In both cases it was noticed that the majority of values were negative, indicating that most exposed regions are hydrophilic. This was as expected since most of the exposed protein surface is usually hydrophilic. It was also observed that there are a few regions with positive peaks for Spatial-Aggregation-Propensity indicating high exposed hydrophobicity. Going from lower radii of patches (5 Å) to the higher radii (10 Å) eliminates some peaks, whereas some other peaks are enhanced. Some peaks were eliminated because in these regions a small hydrophobic patch (with less than 5 Å radius) is surrounded by hydrophilic patches; thus, averaging over 10 Å leads to an effective decrease in hydrophobicity for the region. Whereas in some other regions the Spatial-Aggregation-Propensity at R=10 Å is enhanced because of hydrophobic patches surrounding a similar hydrophobic patch.

Above, the Spatial-Aggregation-Propensity was calculated as an average during the 30 ns simulation run. The results calculated using the simulation were then compared to the Spatial-Aggregation-Propensity of just the X-ray structure, without molecular simulation. The Spatial-Aggregation-Propensity (X-ray) thus was calculated for R=5 Å and for R=10 Å. The Spatial-Aggregation-Propensity (X-ray) was similar to that of the simulation-averaged value, having peaks in the same locations but with differences in the magnitude of the peaks. The differences were higher with the larger radius of patch, R=10 Å. This is probably because the differences are additive when looking at largest patch sizes. These differences arise due to the changing surface exposure of the residues in the dynamic simulation run. Nevertheless, this comparison shows that a good initial estimate of Spatial-Aggregation-Propensity, especially for low radius of patch R, can be obtained from the X-ray structure itself.

The Spatial-Aggregation-Propensity values from the simulation for R=5 Å and 10 Å were mapped onto the antibody structure. In both cases, the antibody surface was colored according to the values of the Spatial-Aggregation-Propensity. At both the radii used in the calculation of Spatial-Aggregation-Propensity (5 Å and 10 Å) it was observed that the surface is predominantly hydrophilic. This is again as expected since most of the protein surface is usually hydrophilic. However, a few hydrophobic regions were noticeable. The contrast between the hydrophobic and hydrophilic regions is more prominent at the higher radii of patch used in the calculation of SAP, R=10 Å. Certain of the identified hydrophobic regions have excellent correlation with regions of the antibody known to interact with other proteins. One patch around residues 234 and 235 in the hinge region is where the Fc-receptor interacts. A second patch around residue 253 corresponds to the region in the Fc fragment where protein A and protein G interact. A significant hydrophobic patch was observed at the end of the Fab fragment corresponds to the region where the antibody binds to antigens. Plots of Spatial-Aggregation-Propensity for R=5 Å and 10 Å respectively, wherein the same correlation of peaks with interacting regions may be observed. The protein interaction sites were obtained from X-ray structure of protein complexes, PDB entries 1T89, 1FC2, and 1FCC (Radaev, *J. Biol. Chem.* 2001, 276(19) 16469; Deisenhofer et al. *Hoppe-Seyler's Z Physiol Chem.* 1978. 359, 975-985; Deisenhofer, *J. Biochemistry.* 1981, 20, 2361-2370; Sauer-Eriksson et al. *Structure.* 1995, 3, 265). The hydrophobic interactions correlate very well with the Spatial-Aggregation-Propensity positive peaks and the hydrophilic interactions correlate well with the Spatial-Aggregation-Propensity negative peaks. Therefore, the Spatial-Aggregation-Propensity parameter can be used to predict the binding sites of proteins as well. In the few exceptions in which residues with low Spatial-Aggregation-Propensity (i.e. close to zero, either positive or negative) also interact, it was observed that the interactions are actually with the atoms of the main backbone chain itself, instead of with the side chains.

Apart from the hydrophobic patches already shown to interact with other proteins discussed above, additional hydrophobic patches on the antibody surface (regions 4 to 6) were identified. Region-5 at the bottom of Fc was significantly hydrophobic, but it is somewhat buried inside, with hydrophilic region on its borders. Similarly regions 4 and 6 are hydrophobic and solvent exposed, but they are facing into the interior of the antibody. Regions 4 and 6 could still be potentially involved in interactions with other proteins if they are exposed due to significant conformational changes or unfolding of the antibody. All of the hydrophobic patches (regions 1 to 6) could also be observed at the smaller patch radius (R=5 Å), although with less contrast compared to the higher patch radius (R=10 Å).

The Spatial-Aggregation-Propensity (X-ray) values which are based on just the X-ray structure were also mapped onto the antibody surface, to compare them with the simulation averaged values. Comparing Spatial-Aggregation-Propensity calculated either through simulation or using just the X-ray structure showed that the hydrophobic regions identified were quite similar. There are of course some differences, such as the intensity of the Protein A interaction patches. Nevertheless, this comparison demonstrates that Spatial-Aggregation-Propensity (Xray) based on just the X-ray structure can be used to obtain a good description of the distribution of hydrophobic patches on the surface. This is important since the atomistic simulation of a full antibody is computationally demanding. For proteins lacking an X-ray structural model, the same Spatial-Aggregation-Propensity parameter can be applied to the structure generated through homology modeling or ab-initio structure prediction. The homology structure was observed to be very similar to the X-ray structure, and its Spatial-Aggregation-Propensity values are also similar to the X-ray structure.

Thus Spatial-Aggregation-Propensity identifies the hydrophobic patches on the surface of the antibody. These patches could be natively exposed or exposed due to dynamic fluctuations or partial unfolding of the antibody. Some of these hydrophobic patches also correlate well with regions interacting with other proteins. In order to test if these hydrophobic patches predicted by Spatial-Aggregation-Propensity are involved in aggregation as well, mutations in these specific regions were performed to change the hydrophobic residues into hydrophilic residues. The resulting antibodies showed less aggregation behavior and improved stability. Apart from identifying aggregation prone residues, it was also observed that the SAP method correctly identifies the regions of the antibody prone to binding with other proteins. Therefore, the method could be broadly applied to all proteins to identify the aggregation prone regions or binding regions with other proteins.

Example 3

Selection of Antibody Sites for Stability Engineering

The residues identified as having high Spatial-Aggregation-Propensities (and therefore being at the center of aggregation prone motifs identified by the inventors) are set forth in Table 1. Given that these are at the center of the motifs, these residues as well as those residues within 5 Å (or 10 Å if a 10 Å window is used in the calculation) may be modified to less hydrophobic residues to reduce aggregation and/or increase stability. Residues were identified for a human IgG1 antibody (with kappa light chain), and the corresponding residues in the different IgG classes are shown in Table 1.

TABLE 1

The aggregation prone motifs in various domains for all IgG class of antibodies. The differences between IgGs are underlined.
Aggregation prone motifs

| Domain | Residue Number | Residue names IgG1 | IgG2 | IgG3 | IgG4 |
|---|---|---|---|---|---|
| $C_{H1}$ | 175 | L | L | L | L |
| Hinge | 234 | L | P | L | F |
|  | 235 | L | V | L | L |
| $C_{H2}$ | 253 | I | I | I | I |
|  | 282 | V | V | V | V |
|  | 291 | P | P | P | P |
|  | 296 | Y | F | Y | F |
|  | 309 | L | V | L | L |
|  | 328 | L | L | L | L |
|  | 329 | P | P | P | P |
|  | 330 | A | A | A | S |
| $C_{H3}$ | 398 | L | L | L | L |
|  | 443 | L | L | L | L |

| Domain | Residue Number | Kappa | Lambda |
|---|---|---|---|
| $C_L$ | 110 | V | K |
|  | 154 | L | P |
|  | 201 | L | — |

Table 1 shows that the motifs are mostly conserved between the different IgGs with a few differences. However, most of the differences are from a hydrophobic amino acid to another hydrophobic amino acid. Therefore, the hydrophobicity of the motif remains intact even with these differences and therefore the other classes with hydrophobic residues at the same position are also aggregation prone motifs. There are a few exceptions to this (A330S, V110K and the deletion of L201) which are not aggregation prone motifs. Apart from these exceptions, the motifs identified here have similar exposed hydrophobicity and higher SAP values for all the IgG class of antibodies.

Table 2 shows hydrophobic residues organized into aggregation prone motifs.

TABLE 2

Fourteen motifs of the constant region of the IgG1 molecule.

| Domain | $SAP_{5Å} > 0.15$ | Residues with (SAP5 Å > 0) within 5 Å of ($SAP_{5Å} > 0.15$) (Aggregation prone motif number) |
|---|---|---|
| $C_{H1}$ (119-224) | 175 LEU | 174 VAL 1 |
|  |  | 175 LEU 1 |
|  |  | 181 TYR 1 |
| Hinge (221-237) | 227 PRO | 226 CYS 2 |
|  | 228 PRO | 227 PRO 2 |
|  | 229 CYS | 228 PRO 2 |
|  | 230 PRO | 229 CYS 2 |
|  | 231 ALA | 230 PRO 2 |
|  | 232 PRO | 231 ALA 2 |
|  | 234 LEU | 232 PRO 2 |
|  | 235 LEU | 234 LEU 3 |
|  |  | 235 LEU 3 |
| $C_{H2}$ (238-345) | 253 ILE | 252 MET 4 |
|  | 282 VAL | 253 ILE 4 |
|  | 291 PRO | 282 VAL 5 |
|  | 296 TYR | 291 PRO 6 |
|  | 309 LEU | 296 TYR 7 |
|  | 329 PRO | 308 VAL 8 |
|  | 330 ALA | 309 LEU 8 |
|  |  | 328 LEU 9 |
|  |  | 329 PRO 9 |
|  |  | 330 ALA 9 |
|  |  | 331 PRO 9 |
| $C_{H3}$ (346-447) | 395 PRO | 395 PRO 10 |
|  | 398 LEU | 396 PRO 10 |
|  | 443 LEU | 397 VAL 10 |
|  |  | 398 LEU 10 |
|  |  | 404 PHE 10 |
|  |  | 443 LEU 11 |

TABLE 2-continued

Fourteen motifs of the constant region of the IgG1 molecule.

| Domain | SAP$_{5Å}$ > 0.15 | Residues with (SAP5 Å > 0) within 5 Å of (SAP$_{5Å}$ > 0.15) (Aggregation prone motif number) |
|---|---|---|
| C$_L$ (110-214) | 110 VAL | 110 VAL 12 |
|  | 154 LEU | 111 ALA 12 |
|  | 201 LEU | 153 ALA 13 |
|  |  | 154 LEU 13 |
|  |  | 201 LEU 14 |

Example 4

Selection of Antibody Sites for Stability Engineering

In order to demonstrate that the aggregation prone motifs identified by their SAP are involved in aggregation and/or instability, mutations were generated in the identified regions to change the hydrophobic residues into hydrophilic residues. Here the selected residues were all changed to lysine. In general, the amino acids which form the general motifs can be replaced by amino acids which are more hydrophilic in the Black and Mould scale, in particular by Thr, Ser, Lys, Gln, Asn, His, Glu, Asp, and Arg. The selected regions were as follows: A1 (L235K), A2 (I253K), A3 (L309K), A4 (L309K, L235K), and A5 (L234K, L235K). The resulting mutant antibodies showed less aggregation behaviour and improved stability as described in Example 6.

Example 5

Expression and Purification of Antibody Variants

The selected residues discussed in Example 4 above were mutated, and the resulting antibody variants were expressed and purified. Vectors that carry the light chain or the heavy chain genes of the human IgG1 Antibody A were obtained by subcloning the genes from proprietary vectors (Novartis) into a gWIZ vector (Genlantis), optimized for high expression from transient transfection. Antibody variants were generated following the Stratagene protocol for site-directed mutagenesis. All constructs were confirmed by DNA sequencing. Plasmid DNA at the mg scale was purified from bacterial cultures with DNA Maxi Prep columns (Invitrogen). The manufacturer's protocols were followed for growth and transient transfection of FreeStyle HEK 293 cells (Invitrogen). In brief, for transfection of 1 L culture, 1 mg total DNA (0.5 mg of the HC and LC vectors each) was incubated with 20 ml OptiPro solution for 15 minutes; at the same time 2 mg of the transfection reagent polyethyleneimine (PEI (Polysciences) at 1 mg/ml) was incubated with 20 ml OptiPro solution for 15 minutes. The PEI solution was then added to the DNA solution, mixed by swirling, and incubated for another 15 minutes. Aliquots of 20 ml PEI/DNA mix were added to 500 ml cell cultures at 1.0×10$^6$ cells/ml. Transfected cells were incubated in a CO$_2$ incubator at 37° C. for 7-9 days.

Antibody wild type and variants were purified from the tissue culture supernatant on a Protein A column (GE Healthcare) with the use of an FPLC AKTA Purifier system (GE Healthcare). Antibodies were eluted from the column with 50 mM citrate buffer pH 3.5, and equilibrated to pH 6.6-7.0 with 1M Tris-HCl pH 9.0. This eluate was passed over a Q Sepharose column (GE Healthcare) to remove negatively charged impurities. At pH 7.0 and below, the antibodies are positively charged and remain in the flow-through, while negatively charged impurities bind to the positively charged matrix of the Q Sepharose column. The solution with purified antibody was concentrated with 30K MWCO filters (Millipore, VWR) and buffer exchanged with 20 mM His buffer pH 6.5 to a final concentration of 150 mg/ml.

As a quality control, aliquots of the purified and concentrated samples were analyzed by SDS-PAGE under non-reducing and reducing conditions. Protein aliquots of 4 μg per sample were incubated in denaturing buffer without or with DTT and resolved on a 10% polyacrylamide gel (Pierce). Variant A1 was compared to wild type also by circular dichroism wherein the spectra were essentially identical showing that the two proteins had essentially the same degree of secondary structure.

Example 6

Biophysical Characterization of Antibody Variants

The stability of the antibody variants was analyzed with three different analytical methods.

Turbidity Assay

A turbidity assay was carried out at 65° C. for up to 4 hours. Antibody A and variants were at a concentration of 150 mg/ml in 20 mM His, pH 6.5, and diluted 15-fold in 15 mM potassium phosphate buffer, pH 6.5 to 10 mg/ml for turbidity assessment. In addition to the qualitative observations, turbidity was quantified after further diluting the samples to 1 mg/ml and recording the absorbance values at 320 nm as shown in Table 3.

TABLE 3

Turbidity assay comparison of Antibody A wild type and variants. Samples at 150 mg/ml were incubated at 65° C. for up to 4 hours.

| Variant | 0 HRS | 1 HR | 2 HRS | 4 HRS |
|---|---|---|---|---|
| WT | 0.02 | 0.06 | 0.27* | *** |
| A1 | 0.01 | 0.03 | 0.04 | 0.19* |
| A2 | 0.01 | 0.04 | 0.07 | ** |
| A3 | 0.01 | 0.03 | 0.05 | ** |
| A4 | 0.01 | 0.04 | 0.04 | 0.13* |
| A5 | 0.01 | 0.04 | 0.09 | 0.14* |

Asterisks indicates the state of the solution at 10 mg/ml, or if the sample had gelified, as follows:
*denotes a liquid, turbid upon dilution;
** denotes gel, clear upon dilution; and
*** denotes a gel, turbid upon dilution. Values without asterisks were liquid, clear upon dilution.
The numbers represent absorbance at 320 nm after further dilution of the samples to 1 mg/ml.

Size Exclusion—High Performance Liquid Chromatography (SEC-HPLC)

As a second and preferred assay, SEC-HPLC was used to determine monomer loss over time in accelerated aggregation experiments. Antibody A wild type and variants were incubated in a thermal cycler (BioRad) at 150 mg/ml at 58° C. for up to 24 hours. For each time point, sample aliquots of 2 μl were diluted 15-fold in 15 mM potassium phosphate buffer, pH 6.5 to a final concentration of 10 mg/ml. Monomers were resolved from non-monomeric species by SEC-HPLC on a TSKgel Super SW3000 column (TOSOH Bioscience), maintained at 22° C., with a mobile phase of 150 mM potassium phosphate, pH 6.5, at a flow rate of 0.2 ml/min. Percent monomer was calculated as the area of the monomeric peak divided by the total area of all peaks detected at 280 nm.

Differential Scanning Microcalorimetry

Third, the thermodynamic stability of antibody A wild type and variants was compared by Differential Scanning Microcalorimetry (DSC, Microcal). MAbs have characteristic DSC thermograms with three melting transitions, if not overlapping: Fab, $C_{H2}$, and $C_{H3}$ (Ionescu et al., J Pharm Sci, v. 97, 1414, 2008; Mimura et al., J Biol Chem, v. 276, 45539, 2001). At the experimental conditions used here, antibody A Fab has a melting transition at 77° C. The $C_{H2}$ and $C_{H3}$ melting temperatures are at 73° C. and 83° C. respectively. Thus, in antibody A, $C_{H2}$ is the antibody domain with the lowest melting temperature.

Antibody A wild type and variants A1-A5 were analyzed at a concentration of 2 mg/ml in 20 mM His pH 6.5 buffer and a heating rate of 1.0 degree per minute. The sample data was analyzed by subtraction of the reference data, normalization to the protein concentration and DSC cell volume, and interpolation of a cubic baseline. The peaks were deconvoluted by non-2-state fit using Microcal Origin 5.0 software. A comparison of the thermograms showed an increase of the $C_{H2}$ melting transition in the variants compared to wild type by 1 to 3 degrees, with the difference most pronounced for the double Variants A4 and A5 (table 4 below).

TABLE 4

$T_m1$ is the melting transition for the $C_{H2}$ domain. $T_m2$ is the melting transition for the Fab domain. $T_m3$ is the melting transition for the $C_{H3}$ domain.

| MAb | $T_m1$ (° C.) | $T_m2$ (° C.) | $T_m3$ (° C.) |
|---|---|---|---|
| WT | 73.5 | 77.3 | 83.6 |
| A1 | 76.0 | 77.8 | 83.5 |
| A2 | 75.0 | 77.5 | 83.4 |
| A3 | 75.5 | 77.6 | 83.4 |
| A4 | 76.2 | 77.7 | 83.1 |
| A5 | 76.3 | 77.9 | 83.3 |

Example 7

Summary

The results from the turbidity, SEC-HPLC and DSC experiments of antibody A wild type and variants are summarized in Table 5.

TABLE 5

Summary of results for antibody A wild type and variants.

| | | | Relative Stability Based on | | |
|---|---|---|---|---|---|
| Variant | Mutation | Domain | Turbidity | HPLC | DSC |
| WT | na | na | ++ | ++ | ++ |
| A1 | L235K | $C_{H2}$ lower hinge | ++++ | +++ | +++ |
| A2 | I253K | $C_{H2}$-$C_{H3}$ junction | +++ | +++ | +++ |
| A3 | L309K | $C_{H2}$ | +++ | +++ | +++ |
| A4 | L235K L309K | $C_{H2}$ | ++++ | ++++ | ++++ |
| A5 | L234K L235K | $C_{H2}$ | ++++ | +++ | ++++ |

Legend:
+ least stable;
++ stable as WT;
+++ more stable;
++++ most stable.

Each of the three single mutants A1, A2, and A3 showed improved stability by each of the three analytical methods. In the turbidity assay, dilution of antibody A wt sample stressed at 65° C. for 2 hrs resulted in clouding of the solution, while the solutions for all variants remained clear. SEC-HPLC results of samples stressed at 58° C. for 24 hrs indicated monomer increase from 91% for wild type to 93-95% for the variants. As the initial monomer population was 99%, the non-monomeric species in the variants decreased up to a half compared to wild type. DSC analysis showed an increase of the melting transition for $C_{H2}$ (the domain with the lowest melting transition in antibody A) from 73° C. for wild type to 75-76° C. for the variants.

Substituting additional high-SAP residues in Variant A1 further improved stability, as evidenced by the Turbidity results and the DSC thermograms for Variants A4 and A5. The SEC-HPLC results showed an improvement over Variant A1 only for Variant A4 (96% monomer after 24-hrs stress) and not for Variant A5 (93% monomer after 24-hrs stress, as Variant A1).

By way of confirmation, similar mutations were generated in a second antibody with the addition of mutation of residues in the CDR regions of the antibody. All but one of the mutations tested improved the stability and/or reduced aggregation. Mutations at one residue in a CDR region did not perform as predicted, however, this may have been because this variant did not express well which may have been due to a defect in folding and therefore had a greater degree of aggregation than the wild-type even before the accelerated aggregation analysis. Thus, all mutations tested in framework and conserved regions produced the predicted result, thereby proving that the SAP algorithm is robust with the sole possible exception of the mutations which are unable to fold properly. However, given that the mutations are all to surface exposed residues and involve substitution with more hydrophilic residues, such folding issues are expected to be rare.

Example 8

Stability Analysis of Additional Antibody Variants

Additional variants were designed and analyzed for improved stability in the first and second antibody. Sites for mutation were based on SAP predictions. The mutations in each variant are listed in Table 6.

TABLE 6

Position of mutated sites in additional variants.

| Variant | Starting Antibody | Rationale | Mutation | Domain |
|---|---|---|---|---|
| A6 | Ab-1 | SAP | L235S | Hinge |
| A7 | Ab-1 | SAP | V282K | $C_H2$ |
| A8 | Ab-1 Var A4 | SAP | V282K L235K L309K | Hinge $C_H2$ |
| B6 | Ab-2 | SAP | L235E | $C_H2$ |

SEC-HPLC was used to determine monomer loss over time in accelerated aggregation experiments. For the first antibody, wild type and variant antibodies were incubated in a thermal cycler (BioRad) at 150 mg/ml at 58° C. for up to 24 hours. For the second antibody, wild type and variant antibodies were incubated in a thermal cycler (BioRad) at 60 mg/ml at 52° C. for up to 36 hours. For each time point, sample aliquots of 2 μl were diluted 15-fold in 15 mM potassium phosphate buffer, pH 6.5 to a final concentration of 10 mg/ml. Monomers were resolved from non-monomeric species by SEC-HPLC on a TSKgel Super SW3000 column (TOSOH Bioscience), maintained at 22° C., with a mobile phase of 150 mM potassium phosphate, pH 6.5, at a flow rate of 0.2 ml/min. Percent monomer was calculated as the area of the monomeric peak divided by the total area of all peaks detected at 280 nm.

Variant A6 showed an increase from 95.5% for wild-type to 96% monomer at 12 hours and an increase from 91% for wild-type to 92% monomer at 24 hours. Variant A7 showed an increase from 96.5% for wild-type to 97.5% monomer at 12 hours and an increase from 91% for wild-type to 94% monomer at 24 hours. Variant A8 showed an increase from 96.5% for wild-type to 98.5% monomer at 12 hours and an increase from 91% for wild-type to 97% monomer at 24 hours. Variant B6 showed no significant difference in percentage monomer at 12 hours, showed an increase from 97.5% for wild-type to 98% monomer at 24 hours, and an increase from 96% for wild-type to 97% monomer at 36 hours.

Example 9

The Role of Protein-Carbohydrate Interactions in SAP and Stability

In this example we determined the effect of glycosylation of an antibody on SAP values. The SAP was determined at R=5 Å for the full antibody both with and without glycosylation. The SAP for antibody with glycosylation was determined from 30 ns molecular dynamics simulation of the full antibody with G0-glycosylation. The SAP for antibody without glycosylation was determined with the same simulation, but where we removed the glycosylation during SAP analysis. The high SAP regions are the most aggregation prone regions. It was observed that the removal of glycosylation significantly increased the SAP in the regions covered by glycosylation, especially for residues F241 and F243. Therefore, removal or displacement of glycosylation led to a significant increase in the aggregation prone regions. These regions could either directly cause aggregation or lower the free energy barrier for unfolding, making the non-glycosylated form less-stable compared to the glycosylated form.

To further explore the role of protein-carbohydrate interactions experimentally, two antibody mutants, F241S F243S (Variant FS) and F241Y F243Y (Variant FY), were generated. Variant FS has phenylalanine residues known to interact with the carbohydrate moiety replaced with polar serine residues that have smaller and non-aromatic side chains (Deisenhofer, *Biochem,* 1981, 20, 2361-70; Krapp et al., *J Mol Biol,* 2003, 325, 979-89). In Variant FY, the same phenylalanine residues are replaced by Tyr residues, which have been suggested to have higher sugar interface propensity (Taroni et al., *Protein Eng,* 2000, 13, 89-98). At the same time, other hydrophobic residues, for example Val264, remain unmodified in this region. Both wild type and Variant FY had very little if any sialylation of their carbohydrates, while nearly 50% of the molecules of Variant FS had at least one sialic acid residue.

The stability of wild type and Variants FS and FY was compared in accelerated aggregation experiments and by differential scanning micro-calorimetry (DSC). Samples at 150 mg/ml were induced to aggregate at 58° C. for up to 36 hrs, and monomer levels were resolved and quantified by size-exclusion high performance liquid chromatography (SEC-HPLC). Wild-type monomer levels gradually decreased from 100 to 96, 91, and 87% for 0, 12, 24, and 36 hrs time points. In comparison, variant FY had reduced monomer levels by 1-3% in the earlier time points but remained at 88% at 36 hrs, within statistical error of wild type. Variant FS was significantly less stable at this temperature showing a monomer decrease from 99% to 39% at 12 hrs, and to 20% at 24 hrs. The 36-hrs samples were not run on SEC-HPLC because of the presence of abundant visible aggregates.

DSC results also differentiated between the variants and wild type. The melting temperature (Tm) of the $C_H2$ domain decreased from 73° C. for wild type to 59° C. for Variant FS. Minor differences in Variant FS, not greater than 1° C., were observed for the melting transitions of Fab and $C_H3$ as well. Although the $C_H2$ melting transition shoulder of Variant FY overlapped that of wild type, the software fitting indicated lowering of the $C_H2$ Tm to 71° C., while the other two Tm's remain unchanged.

A number of additional experiments were carried out to compare Variant FS to wild type and to better understand the observed decrease in stability. Variant FS retained the same β-sheet-rich structure as wild type. The variant had different mobility patterns compared to wild type on reducing as well as native gel electrophoresis. Protease treatment experiments were also carried out to compare protein surface exposure in Variant FS and wild type. Digestion of the antibodies with Glu-C was more efficient (more small fragments) for Variant FS than wild type; that efficiency was largely equalized in the variant and wild type deglycosylated counterparts, although some differences persisted. Furthermore, Variant FS retained full FcRn and partial FcγRIa binding function but lost binding to FcγRII and FcγRIII receptors.

What we claim is:

1. A modified immunoglobulin formulation comprising a modified or isolated immunoglobulin having reduced propensity for aggregation comprising at least one aggregation reducing mutation at a residue in a conserved domain of the immunoglobulin that (i) has a Spatial-Aggregation-Propensity (5 Å radius sphere) of at least 0.15, or (ii) has an Spatial-Aggregation-Propensity (5 Å radius sphere) of greater than 0.0 and is within 5 Å of a residue having a Spatial-Aggregation-Propensity (5 Å radius sphere) of at least 0.15, wherein the at least one aggregation reducing mutation is a substitution with an amino acid residue that lowers the Spatial-Aggregation-Propensity (5 Å radius sphere) of the residue as compared to the unmutated immunoglobulin and the propensity for aggregation that is reduced is aggregation between immunoglobulin molecules in a concentrated, liquid solution, wherein the at least one aggregation reducing mutation is not residue 234(hinge) or 235(hinge), wherein the modified or isolated immunoglobulin is at a concentration of at least 75 mg/ml, wherein at least eighty percent of the modified or isolated immunoglobulin is non-aggregated monomer, and wherein the modified or isolated immunoglobulin comprises a substitution at 309(CH2).

2. The modified immunoglobulin formulation of claim 1 further comprising at least one aggregation reducing mutation residue is selected from the group consisting of residues from an aggregation motif 1: 174($C_{H1}$), 175($C_{H1}$), and 181 ($C_{H1}$); an aggregation motif 2: 226(hinge), 227(hinge), 228 (hinge), 229(hinge), 230(hinge), 231(hinge), and 232(hinge); an aggregation motif 3: 234(hinge) and 235(hinge); an aggregation motif 4: 252($C_{H2}$), and 253($C_{H2}$); an aggregation motif 5: 282($C_{H2}$); an aggregation motif 6: 291($C_{H2}$); an aggregation motif 7: 296($C_{H2}$); an aggregation motif 8: 308($C_{H2}$); an aggregation motif 9: 328($C_{H2}$), 329($C_{H2}$), 330($C_{H2}$), and 331 ($C_{H2}$); an aggregation motif 10: 395($C_{H3}$), 396($C_{H3}$), 397 ($C_{H3}$), 398($C_{H3}$), and 404($C_{H3}$); an aggregation motif 11: 443($C_{H3}$); an aggregation motif 12: 110($C_L$) and 111($C_L$); an aggregation motif 13: 153($C_L$) and 154($C_L$); and an aggregation motif 14: 201($C_L$).

3. The modified immunoglobulin formulation of claim 2 wherein the at least one aggregation reducing mutation residue is (i) selected from the group consisting of residues from an aggregation motif 1: 175($C_{H1}$); an aggregation motif 2: 227(hinge), 228(hinge), and 230(hinge); an aggregation motif 3: 234(hinge) and 235(hinge); an aggregation motif 4: 253($C_{H2}$); an aggregation motif 5: 282($C_{H2}$); an aggregation motif 6: 291($CH_2$); an aggregation motif 7: 296($C_{H2}$); an aggregation motif 9: 329($C_{H2}$) and 330($C_{H2}$); an aggregation motif 10: 395($C_{H3}$) and 398($C_{H3}$); an aggregation motif 11: 443($C_{H3}$); an aggregation motif 12: 110($C_L$); an aggregation motif 13: 154($C_L$); and an aggregation motif 14: 201($C_L$).

4. A modified immunoglobulin formulation comprising a modified or isolated immunoglobulin having reduced propensity for aggregation comprising at least one aggregation reducing mutation at a residue 309(CH2), wherein residue 309 is mutated to a lysine, wherein the modified or isolated immunoglobulin is at a concentration of at least 75 mg/ml, and wherein at least eighty percent of the modified or isolated immunoglobulin is non-aggregated monomer.

5. The modified immunoglobulin formulation of claim 1 wherein the at least one aggregation reducing mutation is a substitution with an amino acid residue that is less hydrophobic than the residue in the unmodified immunoglobulin.

6. The modified immunoglobulin formulation of claim 1 wherein the immunoglobulin further comprises a binding affinity for a target antigen and the binding affinity for the target antigen is at least seventy percent of the binding affinity of the unmutated immunoglobulin for the target antigen.

7. The modified immunoglobulin formulation of claim 1 wherein at least eighty-five percent of the modified or isolated immunoglobulin is non-aggregated monomer.

8. The modified immunoglobulin formulation of claim 1 further comprising a pharmaceutically acceptable excipient.

9. The modified immunoglobulin formulation of claim 1 wherein the immunoglobulin formulation shows at least five percent less aggregate after twenty four hours of accelerated aggregation as compared to the unmutated immunoglobulin under the same conditions.

10. The modified immunoglobulin formulation of claim 1 wherein the immunoglobulin formulation is substantially free of any additive that reduces aggregation of immunoglobulins.

11. A cDNA encoding the immunoglobulin of claim 1.

12. A vector comprising a recombinant polynucleotide encoding the immunoglobulin of claim 1, optionally comprising an inducible promoter operably linked to the polynucleotide.

13. A host cell comprising the vector of claim 12.

14. A method of producing an immunoglobulin with a reduced aggregation propensity comprising:
   (a) providing a culture medium comprising the host cell of claim 13; and
   (b) placing the culture medium in conditions under which the immunoglobulin is expressed; and
   (c) optionally, isolating the immunoglobulin.

15. A modified immunoglobulin formulation comprising a modified or isolated immunoglobulin having reduced propensity for aggregation comprising at least one aggregation reducing mutation at a residue in a conserved domain of the immunoglobulin that (i) has a Spatial-Aggregation-Propensity (5 Å radius sphere) of at least 0.15, or (ii) has an Spatial-Aggregation-Propensity (5 Å radius sphere) of greater than 0.0 and is within 5 Å of a residue having a Spatial-Aggregation-Propensity (5 Å radius sphere) of at least 0.15, wherein the at least one aggregation reducing mutation is a substitution with an amino acid residue that lowers the Spatial-Aggregation-Propensity (5 Å radius sphere) of the residue as compared to the unmutated immunoglobulin and the propensity for aggregation that is reduced is aggregation between immunoglobulin molecules in a concentrated, liquid solution, and a second aggregation reducing mutation at a residue that (i) has a Spatial-Aggregation-Propensity (5 Å radius sphere) of at least 0.15, or (ii) has an Spatial-Aggregation-Propensity (5 Å radius sphere) of greater than 0.0 and is within 5 Å of a residue having a Spatial-Aggregation-Propensity (5 Å radius sphere) of at least 0.15, wherein the second aggregation reducing mutation is a substitution with an amino acid residue that lowers the Spatial-Aggregation-Propensity (5 Å radius sphere) of the residue as compared to the unmutated immunoglobulin, wherein the aggregation reducing mutation and the second aggregation reducing mutation are in different aggregation motifs, wherein the modified or isolated immunoglobulin is at a concentration of at least 75 mg/ml, wherein at least eighty percent of the modified or isolated immunoglobulin is non-aggregated monomer, and wherein the modified or isolated immunoglobulin comprises a substitution at 309(CH2).

16. The modified immunoglobulin formulation of claim 15 wherein the at least one aggregation reducing mutation is a substitution with an amino acid residue that is less hydrophobic than the residue in the unmodified immunoglobulin.

17. The modified immunoglobulin formulation of claim 15 wherein the immunoglobulin further comprises a binding affinity for a target antigen and the binding affinity for the target antigen is at least seventy percent, at least eighty percent, at least ninety percent, at least one hundred percent, or at least one hundred five percent of the binding affinity of the unmutated immunoglobulin for the target antigen.

18. The modified immunoglobulin formulation of claim 1 wherein the immunoglobulin formulation is free of free histidine, saccharides and polyols.

* * * * *

SEQUENCE LISTING

```
<160> NUMBER OF SEQ ID NOS: 19

<210> SEQ ID NO 1
<211> LENGTH: 101
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Ser Leu Ser
         50                  55                  60

Ser Val Val Thr Val Pro Ser Ser Leu Gly Thr Gln Thr Tyr Ile
 65                  70                  75                  80

Cys Asn Val Asn His Lys Pro Ser Asn Thr Lys Val Asp Lys Arg Val
                 85                  90                  95

Glu Pro Lys Ser Cys
            100
```

<210> SEQ ID NO 2
<211> LENGTH: 101
<212> TYPE: PRT
<213> ORGANISM: Homo sapiens

<400> SEQUENCE: 2

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Ser Leu Ser
         50                  55                  60

Ser Val Val Thr Val Pro Ser Ser Asn Phe Gly Thr Gln Thr Tyr Thr
 65                  70                  75                  80

Cys Asn Val Asp His Lys Pro Ser Asn Thr Lys Val Asp Lys Thr Val
                 85                  90                  95

Glu Arg Lys Cys Cys
            100
```

<210> SEQ ID NO 3
<211> LENGTH: 101
<212> TYPE: PRT
<213> ORGANISM: Homo sapiens

<400> SEQUENCE: 3

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Ser Leu Ser
         50                  55                  60

Ser Val Val Thr Val Pro Ser Ser Ser Leu Gly Thr Lys Thr Tyr Thr
 65                  70                  75                  80

Cys Asn Val Asp His Lys Pro Ser Asn Thr Lys Val Asp Lys Arg Val
                 85                  90                  95

Glu Ser Lys Tyr Gly
            100
```

<210> SEQ ID NO 4
<211> LENGTH: 101
<212> TYPE: PRT
<213> ORGANISM: Homo sapiens

<400> SEQUENCE: 4

```
Ala Ser Thr Lys Gly Pro Ser Val Phe Pro Leu Ala Pro Cys Ser Arg
```

```
                1               5                  10                  15
Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Ser Val Val Thr Val Pro Ser Ser Leu Gly Thr Gln Thr Tyr
65                  70                  75                  80

Cys Asn Val Asn His Lys Pro Ser Asn Thr Lys Val Asp Lys Arg Val
                85                  90                  95

Glu Pro Lys Thr Pro
            100

<210> SEQ ID NO 5
<211> LENGTH: 17
<212> TYPE: PRT
<213> ORGANISM: Homo sapiens

<400> SEQUENCE: 5

Asp Lys Thr His Thr Cys Pro Pro Cys Pro Ala Pro Glu Leu Leu Gly
1               5                   10                  15

Gly

<210> SEQ ID NO 6
<211> LENGTH: 13
<212> TYPE: PRT
<213> ORGANISM: Homo sapiens

<400> SEQUENCE: 6

Val Glu Cys Pro Pro Cys Pro Ala Pro Pro Val Ala Gly
1               5                   10

<210> SEQ ID NO 7
<211> LENGTH: 14
<212> TYPE: PRT
<213> ORGANISM: Homo sapiens

<400> SEQUENCE: 7

Pro Pro Cys Pro Ser Cys Pro Ala Pro Glu Phe Leu Gly Gly
1               5                   10

<210> SEQ ID NO 8
<211> LENGTH: 26
<212> TYPE: PRT
<213> ORGANISM: Homo sapiens

<400> SEQUENCE: 8

Leu Gly Thr Thr His Thr Cys Pro Arg Cys Pro Glu Pro Lys Cys Pro
1               5                   10                  15

Arg Cys Pro Ala Pro Glu Leu Leu Gly Gly
            20                  25

<210> SEQ ID NO 9
<211> LENGTH: 106
<212> TYPE: PRT
<213> ORGANISM: Homo sapiens

<400> SEQUENCE: 9

Pro Ser Val Phe Leu Phe Pro Pro Lys Pro Lys Asp Thr Leu Met Ile
1               5                   10                  15
```

```
Ser Arg Thr Pro Glu Val Thr Cys Val Val Asp Val Ser His Glu
         20                  25                  30

Asp Pro Glu Val Lys Phe Asn Trp Tyr Val Asp Gly Val Glu Val His
         35                  40                  45

Asn Ala Lys Thr Lys Pro Arg Glu Glu Gln Tyr Asn Ser Tyr Val Val
 50                  55                  60

Ser Val Leu Thr Val Leu His Gln Asp Trp Leu Asn Gly Lys Glu Tyr
 65                  70                  75                  80

Lys Cys Lys Val Ser Asn Lys Ala Leu Pro Ala Pro Ile Glu Lys Thr
                 85                  90                  95

Ile Ser Lys Ala Lys Gly Gln Pro Arg Glu
            100                 105
```

<210> SEQ ID NO 10
<211> LENGTH: 108
<212> TYPE: PRT
<213> ORGANISM: Homo sapiens

<400> SEQUENCE: 10

```
Pro Ser Val Phe Leu Phe Pro Pro Lys Pro Lys Asp Thr Leu Met Ile
 1               5                  10                  15

Ser Arg Thr Pro Glu Val Thr Cys Val Val Asp Val Ser His Glu
         20                  25                  30

Asp Pro Glu Val Gln Phe Asn Trp Tyr Val Asp Gly Val Glu Val His
         35                  40                  45

Asn Ala Lys Thr Lys Pro Arg Glu Glu Gln Phe Asn Ser Thr Phe Arg
 50                  55                  60

Val Val Ser Val Leu Thr Val Val His Gln Asp Trp Leu Asn Gly Lys
 65                  70                  75                  80

Glu Tyr Lys Cys Lys Val Ser Asn Lys Gly Leu Pro Ala Pro Ile Glu
                 85                  90                  95

Lys Thr Ile Ser Lys Thr Lys Gly Gln Pro Arg Glu
            100                 105
```

<210> SEQ ID NO 11
<211> LENGTH: 106
<212> TYPE: PRT
<213> ORGANISM: Homo sapiens

<400> SEQUENCE: 11

```
Pro Ser Val Phe Leu Phe Pro Pro Lys Pro Lys Asp Thr Leu Met Ile
 1               5                  10                  15

Ser Arg Thr Pro Glu Val Thr Cys Val Val Asp Val Ser Gln Glu
         20                  25                  30

Asp Pro Glu Val Gln Phe Asn Trp Tyr Val Asp Gly Val Glu Val His
         35                  40                  45

Asn Ala Lys Thr Lys Pro Arg Glu Glu Gln Phe Asn Ser Tyr Val Val
 50                  55                  60

Ser Val Leu Thr Val Leu His Gln Asp Trp Leu Asn Gly Lys Glu Tyr
 65                  70                  75                  80

Lys Cys Lys Val Ser Asn Lys Gly Leu Pro Ser Ser Ile Glu Lys Thr
                 85                  90                  95

Ile Ser Lys Ala Lys Gly Gln Pro Arg Glu
            100                 105
```

<210> SEQ ID NO 12
<211> LENGTH: 106
<212> TYPE: PRT

<213> ORGANISM: Homo sapiens

<400> SEQUENCE: 12

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Gln Phe Asn Trp Tyr Val Asp Gly Val Glu Val His
        35                  40                  45

Asn Ala Lys Thr Lys Pro Arg Glu Glu Gln Tyr Asn Ser Tyr Val Val
50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Thr Lys Gly Gln Pro Arg Glu
            100                 105

<210> SEQ ID NO 13
<211> LENGTH: 100
<212> TYPE: PRT
<213> ORGANISM: Homo sapiens

<400> SEQUENCE: 13

Pro Gln Val Tyr Thr Leu Pro Pro Ser Arg Glu Glu Met Thr Lys Asn
1               5                   10                  15

Gln Val Ser Leu Thr Cys Leu Val Lys Gly Phe Tyr Pro Ser Asp Ile
            20                  25                  30

Ala Val Glu Trp Glu Ser Asn Gly Gln Pro Glu Asn Asn Tyr Lys Thr
        35                  40                  45

Thr Pro Pro Val Leu Asp Ser Asp Gly Ser Phe Phe Lys Lys Leu Thr
    50                  55                  60

Val Asp Lys Ser Arg Trp Gln Gln Gly Asn Val Phe Ser Cys Ser Val
65                  70                  75                  80

Met His Glu Ala Leu His Asn His Tyr Thr Gln Lys Ser Leu Ser Leu
                85                  90                  95

Ser Pro Gly Lys
            100

<210> SEQ ID NO 14
<211> LENGTH: 100
<212> TYPE: PRT
<213> ORGANISM: Homo sapiens

<400> SEQUENCE: 14

Pro Gln Val Tyr Thr Leu Pro Pro Ser Arg Glu Glu Met Thr Lys Asn
1               5                   10                  15

Gln Val Ser Leu Thr Cys Leu Val Lys Gly Phe Tyr Pro Ser Asp Ile
            20                  25                  30

Ala Val Glu Trp Glu Ser Asn Gly Gln Pro Glu Asn Asn Tyr Lys Thr
        35                  40                  45

Thr Pro Pro Met Leu Asp Ser Asp Gly Ser Phe Phe Lys Lys Leu Thr
    50                  55                  60

Val Asp Lys Ser Arg Trp Gln Gln Gly Asn Val Phe Ser Cys Ser Val
65                  70                  75                  80

Met His Glu Ala Leu His Asn His Tyr Thr Gln Lys Ser Leu Ser Leu
                85                  90                  95

```
Ser Pro Gly Lys
            100

<210> SEQ ID NO 15
<211> LENGTH: 100
<212> TYPE: PRT
<213> ORGANISM: Homo sapiens

<400> SEQUENCE: 15

Pro Gln Val Tyr Thr Leu Pro Pro Ser Gln Glu Glu Met Thr Lys Asn
1               5                   10                  15

Gln Val Ser Leu Thr Cys Leu Val Lys Gly Phe Tyr Pro Ser Asp Ile
            20                  25                  30

Ala Val Glu Trp Glu Ser Asn Gly Gln Pro Glu Asn Asn Tyr Lys Thr
        35                  40                  45

Thr Pro Pro Val Leu Asp Ser Asp Gly Ser Phe Phe Lys Arg Leu Thr
    50                  55                  60

Val Asp Lys Ser Arg Trp Gln Glu Gly Asn Val Phe Ser Cys Ser Val
65                  70                  75                  80

Met His Glu Ala Leu His Asn His Tyr Thr Gln Lys Ser Leu Ser Leu
                85                  90                  95

Ser Leu Gly Lys
            100

<210> SEQ ID NO 16
<211> LENGTH: 100
<212> TYPE: PRT
<213> ORGANISM: Homo sapiens

<400> SEQUENCE: 16

Pro Gln Val Tyr Thr Leu Pro Pro Ser Arg Glu Glu Met Thr Lys Asn
1               5                   10                  15

Gln Val Ser Leu Thr Cys Leu Val Lys Gly Phe Tyr Pro Ser Asp Ile
            20                  25                  30

Ala Val Glu Trp Glu Ser Ser Gly Gln Pro Glu Asn Asn Tyr Lys Thr
        35                  40                  45

Thr Pro Pro Val Leu Asp Ser Asp Gly Ser Phe Phe Lys Lys Leu Thr
    50                  55                  60

Val Asp Lys Ser Arg Trp Gln Gln Gly Asn Ile Phe Ser Cys Ser Val
65                  70                  75                  80

Met His Glu Ala Leu His Asn His Phe Thr Gln Lys Ser Leu Ser Leu
                85                  90                  95

Ser Pro Gly Lys
            100

<210> SEQ ID NO 17
<211> LENGTH: 7
<212> TYPE: PRT
<213> ORGANISM: Saccharomyces cerevisiae

<400> SEQUENCE: 17

Gly Asn Asn Gln Gln Asn Tyr
1               5

<210> SEQ ID NO 18
<211> LENGTH: 7
<212> TYPE: PRT
<213> ORGANISM: Homo sapiens

<400> SEQUENCE: 18
```

```
Lys Leu Val Phe Phe Ala Glu
1               5

<210> SEQ ID NO 19
<211> LENGTH: 11
<212> TYPE: PRT
<213> ORGANISM: Homo sapiens

<400> SEQUENCE: 19

Val His His Gln Lys Leu Val Phe Phe Ala Glu
1               5                   10
```